(12) United States Patent
Kai et al.

(10) Patent No.: US 9,290,498 B2
(45) Date of Patent: Mar. 22, 2016

(54) ORGANIC ELECTROLUMINESCENT DEVICE HAVING AN ELECTRON- AND/OR EXCITON-BLOCKING LAYER COMPRISING AN INDOLOCARBAZOLE COMPOUND

(75) Inventors: Takahiro Kai, Kitakyushu (JP);
Toshihiro Yamamoto, Kitakyushu (JP);
Masaki Komori, Kitakyushi (JP);
Kazuaki Yoshimura, Kitakyushu (JP);
Taishi Tsuji, Tsurugashima (JP);
Yasuhiro Takahashi, Tsurugashima (JP); Toshinao Yuki, Yonezawa (JP);
Yusuke Nakajima, Yonezawa (JP)

(73) Assignees: NIPPON STEEL & SUMIKIN CHEMICAL CO., LTD., Tokyo (JP);
PIONEER CORPORATION, Kanagawa (JP); TOHOKU PIONEER CORPORATION, Yamagata (JP)

( * ) Notice: Subject to any disclaimer, the term of this patent is extended or adjusted under 35 U.S.C. 154(b) by 697 days.

(21) Appl. No.: 13/502,520

(22) PCT Filed: Oct. 19, 2010

(86) PCT No.: PCT/JP2010/068322
§ 371 (c)(1),
(2), (4) Date: Apr. 17, 2012

(87) PCT Pub. No.: WO2011/049063
PCT Pub. Date: Apr. 28, 2011

(65) Prior Publication Data
US 2012/0205640 A1   Aug. 16, 2012

(30) Foreign Application Priority Data

Oct. 23, 2009 (JP) .................. 2009-244360

(51) Int. Cl.
*H01L 51/54* (2006.01)
*C09K 11/06* (2006.01)
*C07D 487/04* (2006.01)
*H01L 51/00* (2006.01)
*H01L 51/50* (2006.01)

(52) U.S. Cl.
CPC .......... *C07D 487/04* (2013.01); *H01L 51/0072* (2013.01); *H01L 51/5096* (2013.01)

(58) Field of Classification Search
None
See application file for complete search history.

(56) References Cited

U.S. PATENT DOCUMENTS

| 5,942,340 A * | 8/1999 | Hu et al. .................. 428/690 |
| 2008/0220285 A1* | 9/2008 | Vestweber et al. ............ 428/690 |

FOREIGN PATENT DOCUMENTS

| JP | 7-157473 A | 6/1995 |
| JP | 11-162650 A | 6/1999 |
| JP | 11-176578 A | 7/1999 |
| JP | 2003-229275 A | 8/2003 |
| JP | 2003-261560 A | 9/2003 |
| JP | 2005-129310 A | 5/2005 |
| JP | 2005-285410 A | 10/2005 |
| JP | 2007-43062 A | 2/2007 |
| WO | WO-2009/104563 A1 | 8/2009 |
| WO | WO-2010/113761 A1 | 10/2010 |

OTHER PUBLICATIONS

International Search Report for the Application No. PCT/JP2010/068322 mailed Dec. 7, 2010.
Chopra, Neetu et al., "High efficiency blue phosphorescent organic light-emitting device", Applied Physics Letters, 2008, vol. 93, pp. 143307-1-143307-3.
Holmes, R. J. et at, "Efficient, deep-blue organic electrophosphorescence by guest charge trapping", Applied Physics Letters, 2003, vol. 83, No. 18, pp. 3818-3820.

* cited by examiner

*Primary Examiner* — Andrew K Bohaty
(74) *Attorney, Agent, or Firm* — Cheng Law Group, PLLC

(57) ABSTRACT

Disclosed is an organic electroluminescent device (organic EL device) which is improved in luminous efficiency, fully secure of driving stability, and of a simple configuration. The organic EL device comprises organic layers comprising a hole-transporting layer and a light-emitting layer sandwiched between an anode and a cathode. The light-emitting layer contains a fluorescent light-emitting material and an electron- and/or exciton-blocking layer containing an indolocarbazole derivative represented by general formula (2) is disposed between the hole-transporting layer and the light-emitting layer so as to be adjacent to the light-emitting layer. In general formula (2), ring B is a heterocyclic ring fused to the adjacent rings and represented by formula (1c), Z is an n-valent aromatic hydrocarbon group or aromatic heterocyclic group, and n is 1 or 2.

9 Claims, 2 Drawing Sheets

ORGANIC ELECTROLUMINESCENT DEVICE HAVING AN ELECTRON- AND/OR EXCITON-BLOCKING LAYER COMPRISING AN INDOLOCARBAZOLE COMPOUND

TECHNICAL FIELD

This invention relates to an organic electroluminescent device containing an indolocarbazole compound and, more particularly, to a thin film type device which emits light upon application of an electric field to a light-emitting layer composed of an organic compound.

BACKGROUND TECHNOLOGY

An organic electroluminescent device (hereinafter referred to as organic EL device) in the simplest structure is generally constituted of a pair of counter electrodes between which a light-emitting layer is sandwiched. The organic EL device functions by utilizing the following phenomenon; upon application of an electric field between the electrodes, electrons are injected from the cathode and holes are injected from the anode and they recombine in the light-emitting layer with emission of light.

In recent years, organic thin films have been utilized in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (Alq3) are disposed between the electrodes. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

PRIOR ART TECHNICAL DOCUMENTS

Patent Documents

Patent document 1: JP H07-157473 A
Patent document 2: JP H11-162650 A
Patent document 3: JP H11-176578 A

Non-Patent Documents

Non-patent document 1: APPLIED PHYSICS LETTERS 2003, 83, 3818
Non-patent document 2: APPLIED PHYSICS LETTERS 2008, 93, 143307

A high luminous efficiency can be obtained from an organic EL device when holes and electrons are injected from the electrodes to the light-emitting layer in good balance and they recombine efficiently in the light-emitting layer. In other words, when injection of both electric charges to the light-emitting layer goes off balance or transport of both electric charges in the light-emitting layer goes off balance, leakage of electric charges to the transporting layers occurs and the probability of recombination in the light-emitting layer is reduced. Moreover, under the condition wherein the balance of electric charges is disturbed, the region for recombination of electric charges in the light-emitting layer becomes limited to a narrow region in the vicinity of the boundary with the transporting layer. In a case such as this, leakage of excitons from the light-emitting layer to the transporting layer occurs and this leads to a reduction in the luminous efficiency. In particular, leakage of electrons and excitons to the hole-transporting layer reduces the luminous efficiency and, at the same time, shortens the life of the device due to degradation of a hole-transporting material. Thus, the aforementioned balancing of electric charges during injection and transportation has become a problem of critical importance.

To solve the aforementioned problem, patent document 1 discloses an example in which N,N'-diphenyl-N,N'-bis(3-methylphenyl)-1,1'-biphenyl-4,4'-diamine (TPD) is used as an electron-blocking layer.

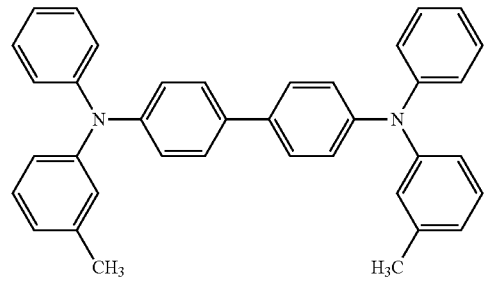 [SMILES: Cc1cccc(N(c2ccccc2)c2ccc(-c3ccc(N(c4ccccc4)c4cccc(C)c4)cc3)cc2)c1]

Further, non-patent documents 1 and 2 disclose examples in which 1,3-dicarbazolylbenzene (mCP) is used as an electron-blocking layer or an exciton-blocking layer.

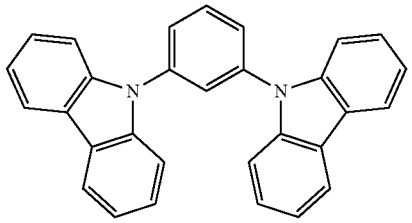 [SMILES: c1cc(-n2c3ccccc3c3ccccc32)cc(-n2c3ccccc3c3ccccc32)c1]

However, the devices comprising the aforementioned organic layers have problems in that they require high driving voltage and fail to exhibit practical luminous characteristics and driving life due to a lack of durability in the compounds used.

That is to say, although blocking leakage of electrons and/or excitons to the hole-transporting layer by inserting an organic layer between the hole-transporting layer and the light-emitting layer is known as a method for realizing an organic EL device exhibiting good light emission and life characteristics, none of known materials is capable of performing this function on a practical level. As the organic layer to be inserted between the hole-transporting layer and the light-emitting layer is intended for blocking leakage of electrons and/or excitons to the hole-transporting layer, it is called an electron-blocking layer or an exciton-blocking layer. The electron- and/or exciton-blocking layer as used in this specification refers to this organic layer. Hereinafter, the electron- and/or exciton-blocking layer is also referred to as EB layer. Thus, the EB layer means one or both of the electron-blocking and exciton-blocking layers.

Meanwhile, patent documents 2 and 3 disclose the indolocarbazole compounds illustrated below. Although these documents disclose that the indolocarbazole compounds are incorporated as charge-transporting components and recommend that the compounds are used as materials for the hole-injecting layer or the hole-transporting layer, they do not teach their use as materials for the EB layer to be disposed between the light-emitting layer and the hole-transporting layer so as to be adjacent to the light-emitting layer.

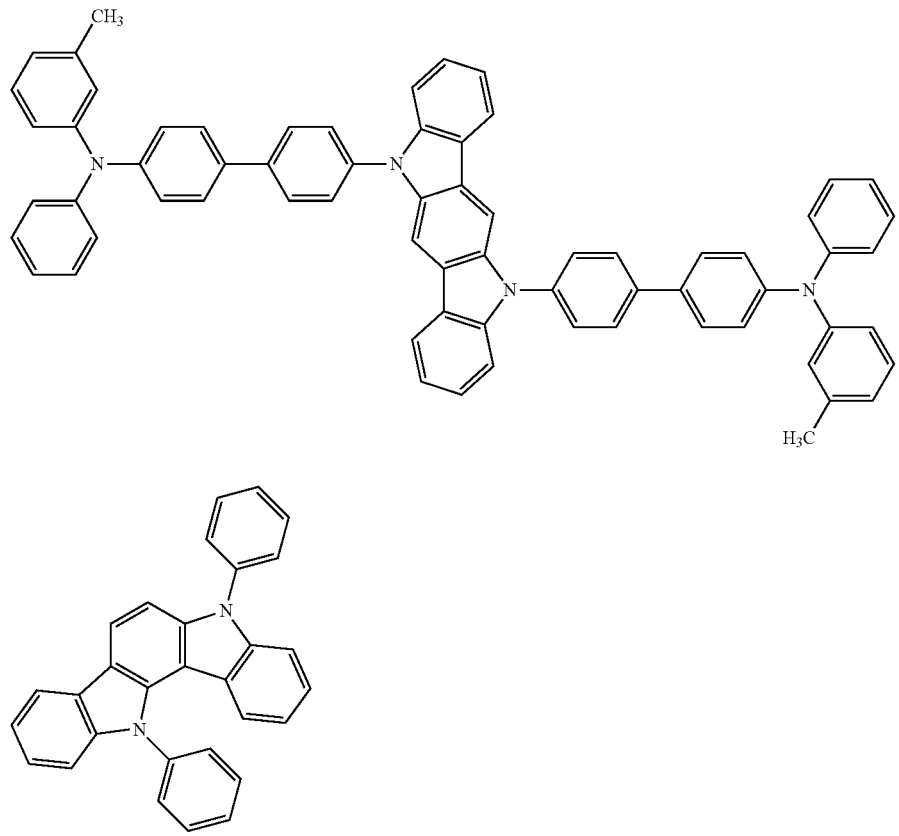 [SMILES: Cc1cccc(N(c2ccccc2)c2ccc(-c3ccc(-n4c5ccccc5c5cc6c(cc54)c4ccccc4n6-c4ccc(-c5ccc(N(c6ccccc6)c6cccc(C)c6)cc5)cc4)cc3)cc2)c1 ; c1ccc(-n2c3ccccc3c3c2ccc2c4ccccc4n(-c4ccccc4)c23)cc1]

Further, the patent documents disclose the characteristics of organic EL devices using those indolocarbazole compounds in the hole-transporting layer. However, the devices still have problems in that they require high driving voltage and exhibit poor life characteristics and it is hard to say that the devices are satisfactory for practical use in light emission and life characteristics.

SUMMARY OF THE INVENTION

In applications of organic EL devices to display devices such as flat panel displays, it is necessary to enhance the luminous efficiency of the device and, at the same time, to fully secure the driving stability of the device. Under the aforementioned circumstances, an object of this invention is to provide an organic EL device exhibiting such luminous efficiency and driving stability as to be practically useful and to provide a compound suitable therefor.

Means to Solve the Problems

The inventors of this invention have conducted intensive studies, found that the use of an indolocarbazole compound of specified structure in the EB layer of an organic EL device can solve the aforementioned problems, and completed this invention.

Accordingly, this invention relates to an organic electroluminescent device comprising organic layers comprising at least a hole-transporting layer and a light-emitting layer sandwiched between an anode and a cathode wherein the light-emitting layer contains a fluorescent light-emitting material and an electron- and/or exciton-blocking layer (EB layer) containing an indolocarbazole compound represented by the following general formula (1) is disposed between the hole-transporting layer and the light-emitting layer so as to be adjacent to the light-emitting layer.

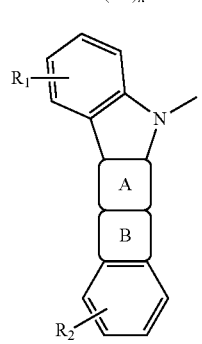

(1)

$$Z-(Y)_n$$

(1a)

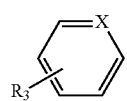

(1b)

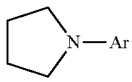
(1c)

In general formula (1), Z is an n-valent aromatic hydrocarbon group of 6 to 50 carbon atoms or an n-valent aromatic heterocyclic group of 3 to 50 carbon atoms; Y is a group represented by formula (1a); n is an integer of 1 to 6 and Y's may be identical with or different from each other when n is 2 or more.

In formula (1a), ring A is an aromatic or heterocyclic ring fused to the adjacent rings and represented by formula (1b) and ring B is a heterocyclic ring fused to the adjacent rings and represented by formula (1c); each of $R_1$ and $R_2$ is independently a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms.

In formula (1b), X is a methine group or a nitrogen atom, $R_3$ is a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms and $R_3$ may be fused to a ring containing X to form a fused ring.

In formula (1c), Ar is an aromatic hydrocarbon group of 6 to 50 carbon atoms or an aromatic heterocyclic group of 3 to 50 carbon atoms.

An example of the indolocarbazole compound represented by general formula (1) is an indolocarbazole compound represented by the following general formula (2).

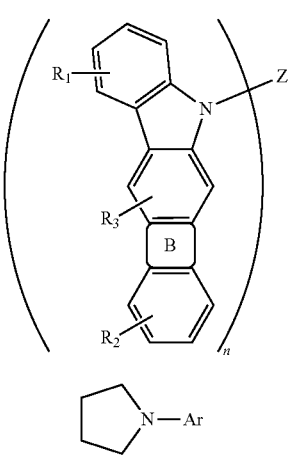
(2)

In general formula (2), ring B is a heterocyclic ring fused to the adjacent rings and represented by general formula (1c); Z, $R_1$, and $R_2$ have the same meaning as those in general formula (1); $R_3$ is a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; n is an integer of 1 or 2.

An example of the indolocarbazole compound represented by general formula (2) is an indolocarbazole compound selected from compounds represented by general formulas (3) to (6).

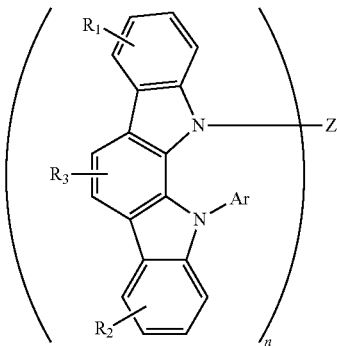
(3)

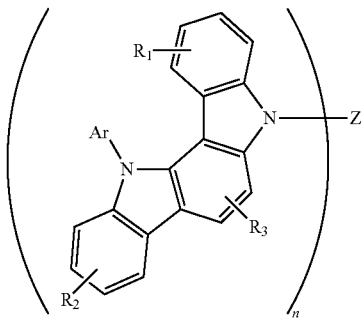
(4)

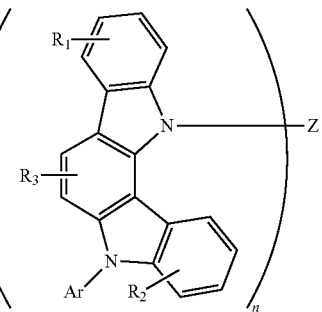
(5)

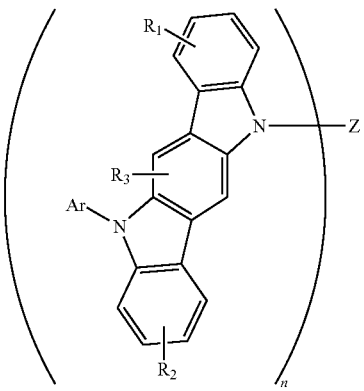
(6)

In general formulas (3) to (6), Z, Ar, $R_1$, $R_2$, $R_3$, and n have the same meaning as those in general formula (2).

In the aforementioned organic electroluminescent device, at least one kind of fluorescent light-emitting material may be incorporated in the light-emitting layer; however, it is preferable to use a fluorescent light-emitting material as a fluorescent dopant and as an electron-transporting host material. In such a case, the fluorescent light-emitting material or the electron-transporting host material may be a single compound or a mixture.

It is preferable that the aforementioned organic electroluminescent device further comprises an electron-transporting layer and at least one of the materials to be used therein has an electron mobility of $1\times10^{-7}$ cm$^2$/V·s or more.

The LUMO energy of an indolocarbazole compound to be incorporated in the aforementioned EB layer is preferably higher than the LUMO energy of a fluorescent light-emitting material to be incorporated in the light-emitting layer present adjacent to the EB layer. Furthermore, the LUMO energy of the indolocarbazole compound is preferably −1.2 eV or more. The said fluorescent light-emitting material may be a single compound or a mixture. In the case of a mixture, the said LUMO energy is induced from the LUMO energy of the main component of the mixture. In the case where the said fluorescent light-emitting material is used as a fluorescent dopant in combination with an electron-transporting host material, the LUMO energy in question is induced from the LUMO energy of the electron-transporting host material and in the case where the electron-transporting host material is a mixture, the LUMO energy in question is induced from the LUMO energy of the main component of the mixture.

Further, the HOMO energy of a hole-transporting material to be incorporated in the hole-transporting layer is preferably higher than the HOMO energy of an indolocarbazole compound to be incorporated in the aforementioned EB layer. Further, the HOMO energy of a hole-transporting material to be incorporated in the hole-transporting layer present adjacent to the anode or the hole-injecting layer is preferably −4.8 eV or more.

PREFERRED EMBODIMENTS OF THE INVENTION

Figure 1:
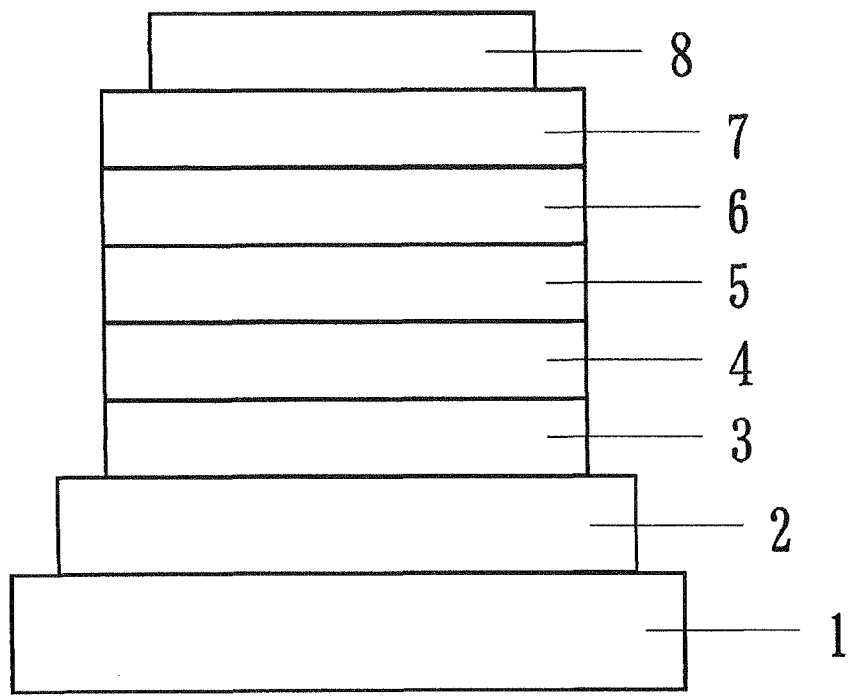
FIG. 1 shows the cross section of an example of an organic EL device.

An organic EL device according to this invention comprises organic layers comprising a plurality of layers including at least a hole-transporting layer and a light-emitting layer sandwiched between an anode and a cathode. In addition, the device comprises an EB layer adjacent to the light-emitting layer on the side of the hole-transporting layer and the hole-transporting layer is disposed on the side of the anode when viewed from the EB layer. The light-emitting layer contains a fluorescent light-emitting material while the EB layer contains an indolocarbazole compound represented by the aforementioned general formula (1).

Some of the indolocarbazole compounds represented by general formula (1) are known in the aforementioned patent documents and elsewhere and the mode of usage differs from compound to compound. However, any of those indolocarbazole compounds, if known as a hole-transporting material, can be used advantageously.

An indolocarbazole compound useful for this invention is represented by general formula (1) wherein Z is an n-valent aromatic hydrocarbon group of 6 to 50 carbon atoms or an n-valent aromatic heterocyclic group of 3 to 50 carbon atoms, n is an integer of 1 to 6, and Y is a group having an indolocarbazole skeleton represented by formula (1a). The aromatic hydrocarbon group and the aromatic heterocyclic group may or may not have a substituent.

Preferable examples of the aromatic hydrocarbon groups and aromatic heterocyclic groups having no substituent include n-valent groups formed by removing n hydrogen atoms from benzene, pyridine, pyrimidine, triazine, indole, carbazole, naphthalene, quinoline, isoquinoline, quinoxaline, and naphthyridine or from aromatic compounds in which a plurality of the foregoing compounds are linked together. More preferable examples include n-valent groups formed by removing n hydrogen atoms from benzene, pyridine, pyrimidine, triazine, indole, carbazole, and naphthalene or from aromatic compounds in which a plurality of the foregoing compounds are linked together. In the case where an n-valent group is derived from an aromatic compound in which a plurality of aromatic rings are linked together, the number of linked aromatic rings is preferably 2 to 10, more preferably 2 to 7. In this case, the position where the n-valent group is linked to Y is not limited and it may be on a terminal ring or on a ring in the middle.

In the case where the n-valent group is a divalent group formed from an aromatic compound in which a plurality of aromatic rings are linked together, such divalent groups are represented by the following formulas (11) to (13).

(11)

(12)

(13)

(Each of Ar$_1$ to Ar$_6$ is an unsubstituted monocyclic or fused aromatic ring.)

Specific examples of groups formed by removing hydrogen atoms from aromatic compounds in which a plurality of aromatic rings are linked together include n-valent groups formed by removing n hydrogen atoms from biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, and diphenylnaphthalene.

In the case where the aforementioned aromatic hydrocarbon group or aromatic heterocyclic group has a substituent, examples of such a substituent include an alkyl group of 1 to 4 carbon atoms, an alkoxyl group of 1 to 2 carbon atoms, an acetyl group, and a diarylamino group of 6 to 24 carbon atoms. More preferable examples include a methyl group and a diphenylamino group. A group formed from an aromatic compound in which a plurality of aromatic rings are linked together may have a substituent.

In the case where the aforementioned aromatic hydrocarbon group or aromatic heterocyclic group has a substituent, the total number of substituents is 1 to 10, preferably 1 to 6, more preferably 1 to 4. In the case where the aforementioned aromatic hydrocarbon group or aromatic heterocyclic group has two or more substituents, the substituents may be identical with or different from one another. In counting the number of carbon atoms in the aforementioned aromatic hydrocarbon group or aromatic heterocyclic group, the number of carbon atoms in the substituents is included.

In general formula (1), n is an integer of 1 to 6, preferably 1 to 4, more preferably 1 to 3.

In general formula (1), Y is represented by formula (1a) and ring A in formula (1a) is represented by formula (1b). In formula (1b), X is a methine group or a nitrogen atom and $R_3$ is a hydrogen atom, an aliphatic hydrocarbon group of 1 to 10 carbon atoms, an aromatic hydrocarbon group of 6 to 12 carbon atoms, an aromatic heterocyclic group of 3 to 11 carbon atoms, or a group to be fused to a six-membered ring containing X. In the case where $R_3$ is a group to be fused to a six-membered ring containing X, the group in question may be a ring obtained by removing the six-membered ring containing X from the ring formed by fusion; examples of such a ring include a pyrrole ring, a furan ring, a thiophene ring, an indole ring, a benzofuran ring, a benzothiophene ring, a benzene ring, and a naphthalene ring and these rings may have a substituent. A preferable example is an indole ring which optionally has a substituent and it preferably forms a carbazole ring by fusing to a six-membered ring containing X. Fusion of $R_3$ to a six-membered ring containing X can occur in the case where the carbon atom adjacent to the position where substitution of $R_3$ occurs has a replaceable hydrogen atom and formation of a carbazole ring is limited to the case where X is a methine group.

In formula (1a), ring B is represented by formula (1c). In formula (1c), Ar is an aromatic hydrocarbon group of 6 to 50 carbon atoms or an aromatic heterocyclic group of 3 to 50 carbon atoms. The aromatic hydrocarbon group and the aromatic heterocyclic group may or may not have a substituent. Preferable examples of these groups are the same as those of the aforementioned group Z in the case where n is 1. Further, the position of substitution of N and Ar in formula (1c) is not limited Preferable examples of the aromatic hydrocarbon group and aromatic heterocyclic group having no substituent include monovalent groups derived from benzene, pyridine, pyrimidine, triazine, indole, carbazole, naphthalene, quinoline, isoquinoline, quinoxaline, and naphthyridine. More preferable examples include monovalent groups derived from benzene, pyridine, pyrimidine, triazine, indole, carbazole, and naphthalene. Preferable examples also include monovalent groups derived from aromatic compounds in which a plurality of the foregoing aromatic rings are linked together; concretely, monovalent groups derived from biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, and diphenylnaphthalene. In the case where any of the aforementioned groups has a substituent, such a substituent is preferably an alkyl group of 1 to 4 carbon atoms, an alkoxyl group of 1 to 2 carbon atoms, an acetyl group, or a diarylamino group of 6 to 24 carbon atoms, more preferably a methyl group or a diphenylamino group.

In formula (1a), each of $R_1$ and $R_2$ is independently a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; preferably, a hydrogen atom, an alkyl group of 1 to 4 carbon atoms, a phenyl group, a pyridyl group, a pyrimidyl group, a triazyl group, a naphthyl group, a biphenylyl group, a bipyrimidyl group, or a carbazolyl group; more preferably, a hydrogen atom, a phenyl group, or a carbazolyl group.

Further, in the case where each of the aforementioned $R_1$, $R_2$, and $R_3$ is an aliphatic hydrocarbon group of 1 to 10 carbon atoms, an aromatic hydrocarbon group of 6 to 12 carbon atoms, or an aromatic heterocyclic group of 3 to 11 carbon atoms, preferable groups are common to these three groups.

A preferable example of the indolocarbazole compound represented by the aforementioned general formula (1) is an indolocarbazole compound represented by general formula (2).

In formula (2), ring B is a heterocyclic ring fused to the adjacent rings and represented by formula (1c). Ring B or formula (1c) here has the same meaning as ring B or formula (1c) in general formula (1). Moreover, Z, Ar, $R_1$, and $R_2$ here respectively have the same meaning as Z, Ar, $R_1$, and $R_2$ in general formula (1). The group $R_3$ is a hydrogen atom, an alkyl group of 1 to 10 carbon atoms, an aromatic hydrocarbon group of 6 to 12 carbon atoms, or an aromatic heterocyclic group of 3 to 11 carbon atoms. It is preferable that the aforementioned aromatic hydrocarbon group and aromatic heterocyclic group here do not have a fused ring structure. The symbol n is an integer of 1 or 2.

Preferred as the indolocarbazole compound represented by the aforementioned general formula (2) is an indolocarbazole compound represented by any one of general formulas (3) to (6).

In general formulas (3) to (6), Z, Ar, $R_1$, $R_2$, $R_3$, and n have the same meaning as those in general formula (2).

The indolocarbazole compounds represented by general formulas (1) to (6) can be synthesized by known methods.

For example, the indolocarbazole skeleton of the indolocarbazole compound represented by general formula (3) may be synthesized by the reaction shown below with reference to a synthetic example described in Synlett., 2005, No. 1, pp. 42-48.

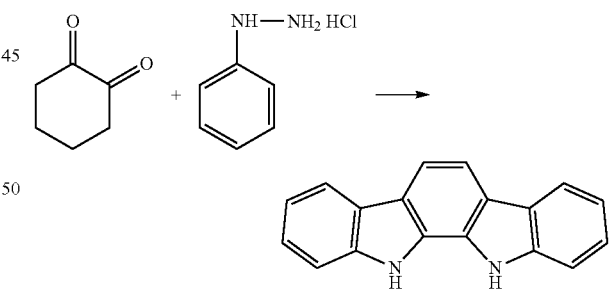

Further, the indolocarbazole skeletons represented by general formulas (4) and (5) may be synthesized by the reactions shown below with reference to synthetic examples described in The Journal of Organic Chemistry, 2007, 72(15), 5886 and Tetrahedron, 1999, 55, p. 2371.

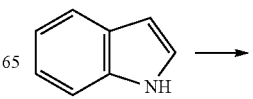

-continued

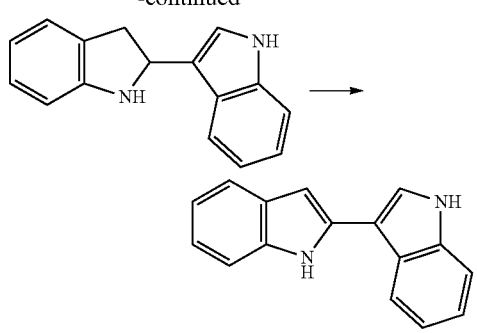

Still further, the indolocarbazole skeleton represented by general formula (6) may be synthesized by the reaction shown below with reference to a synthetic example described in Archiv der Pharmazie (Weinheim, Germany), 1987, 320 (3), pp. 280-282.

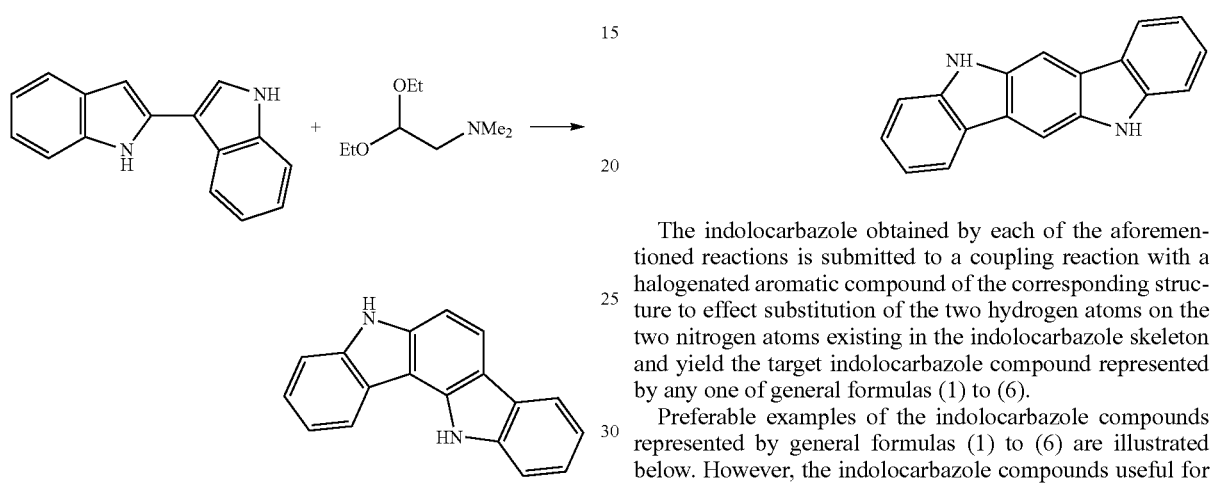

The indolocarbazole obtained by each of the aforementioned reactions is submitted to a coupling reaction with a halogenated aromatic compound of the corresponding structure to effect substitution of the two hydrogen atoms on the two nitrogen atoms existing in the indolocarbazole skeleton and yield the target indolocarbazole compound represented by any one of general formulas (1) to (6).

Preferable examples of the indolocarbazole compounds represented by general formulas (1) to (6) are illustrated below. However, the indolocarbazole compounds useful for this invention are not limited thereto.

1-1

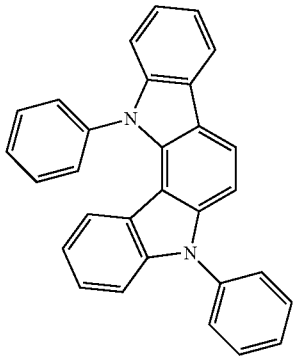

1-2

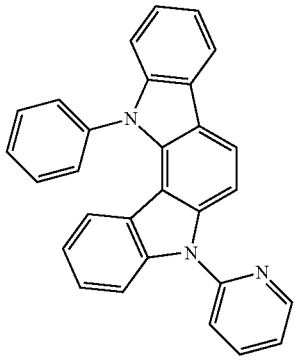

1-3

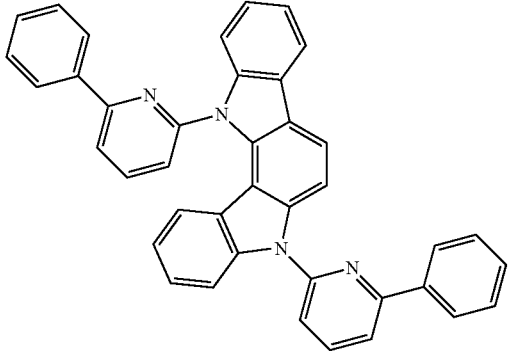

1-4

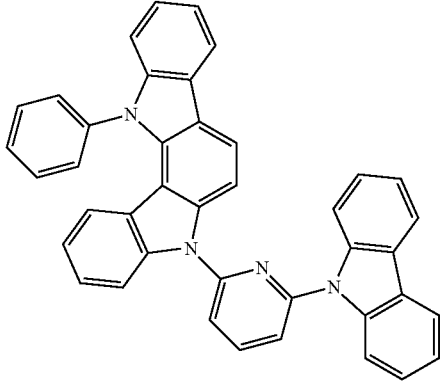

-continued
1-5
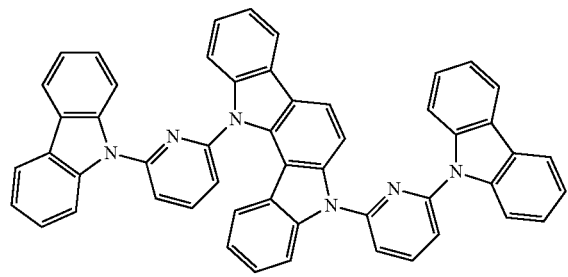
1-6
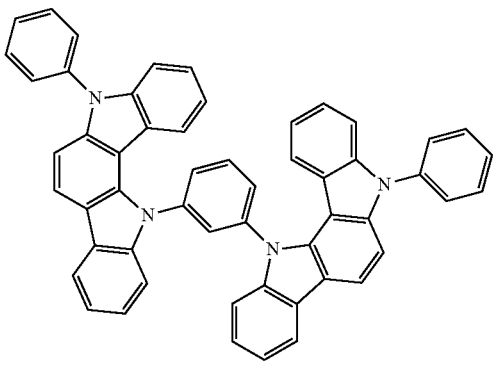
1-7
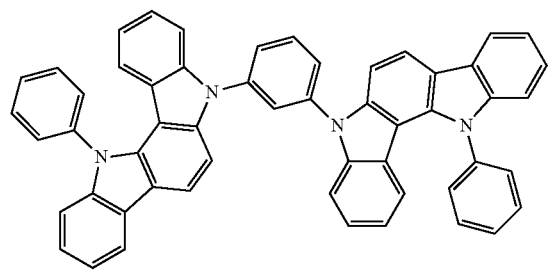
1-8
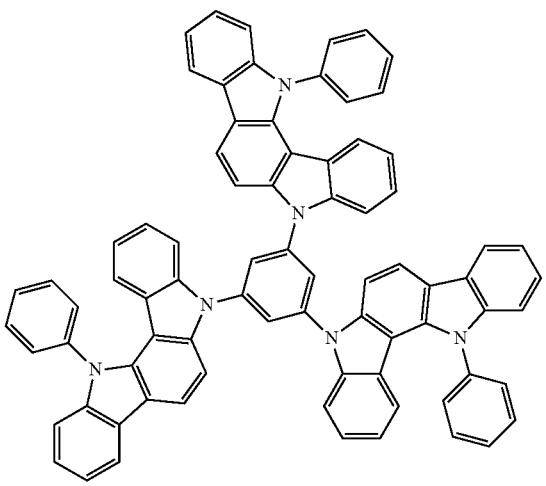
1-9
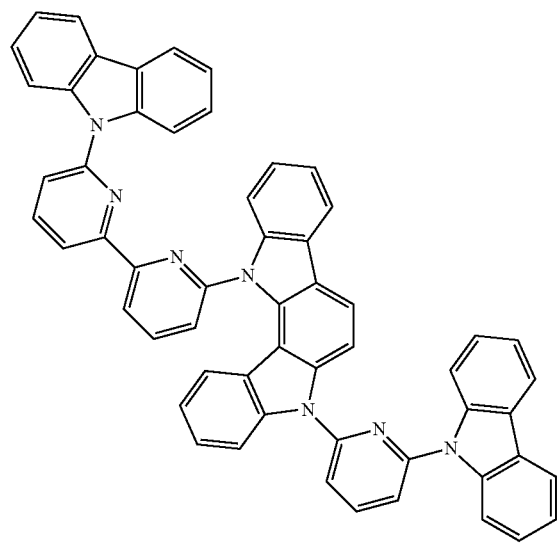
1-10
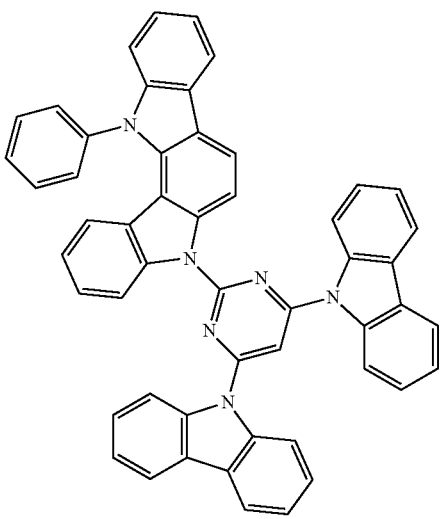

-continued
1-11
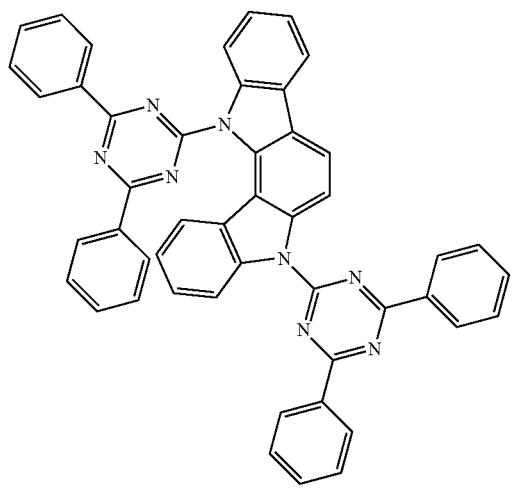
1-12
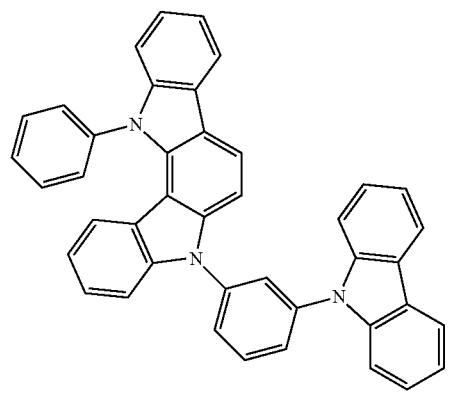
1-13
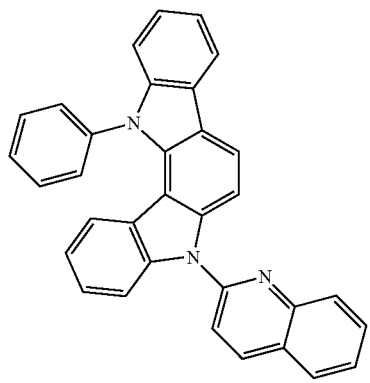
1-14
1-15
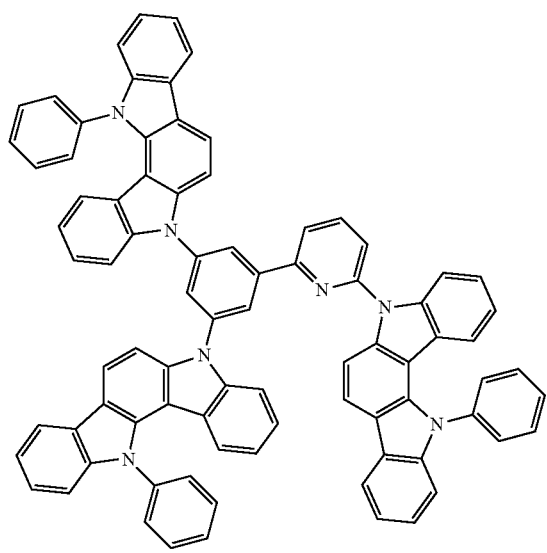
1-16
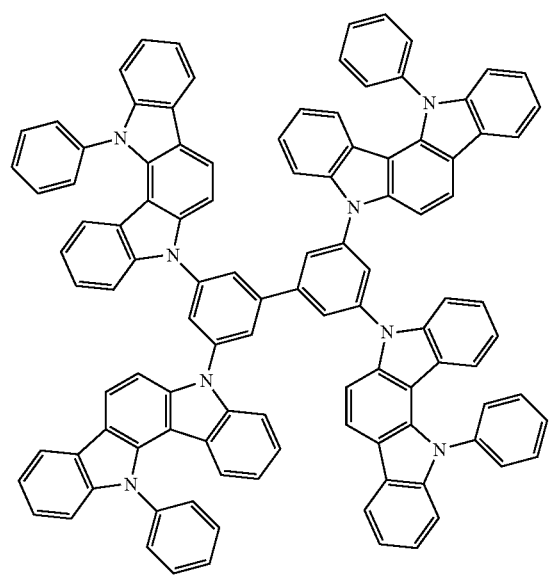

-continued
1-17
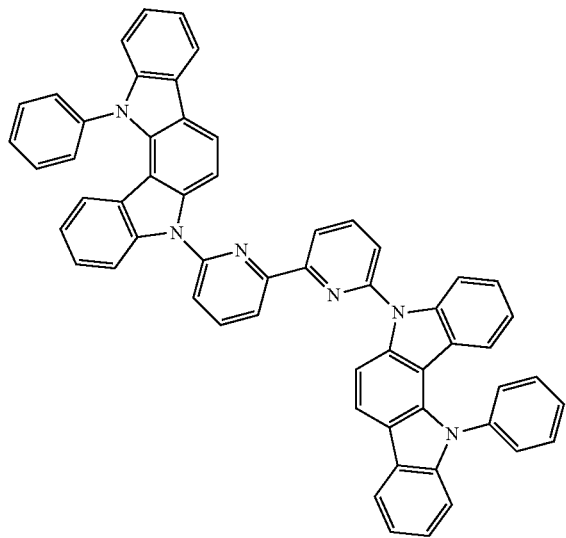
1-18
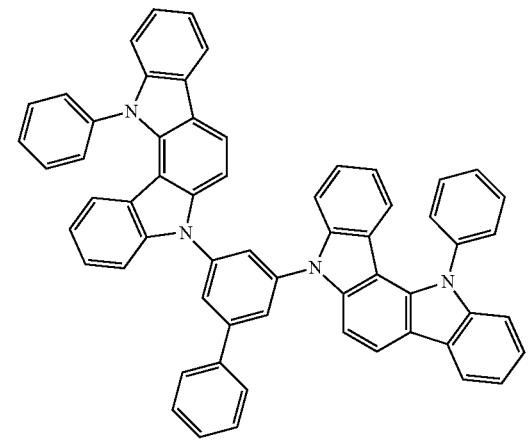
1-19
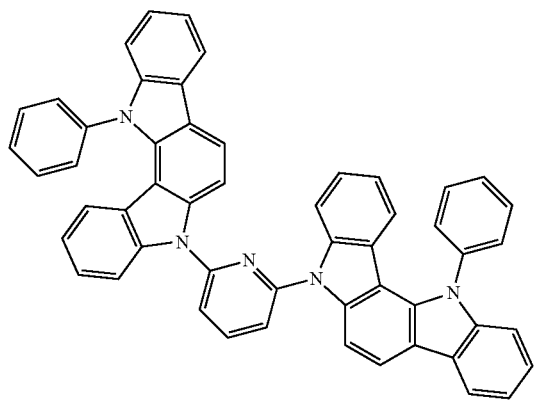
1-20
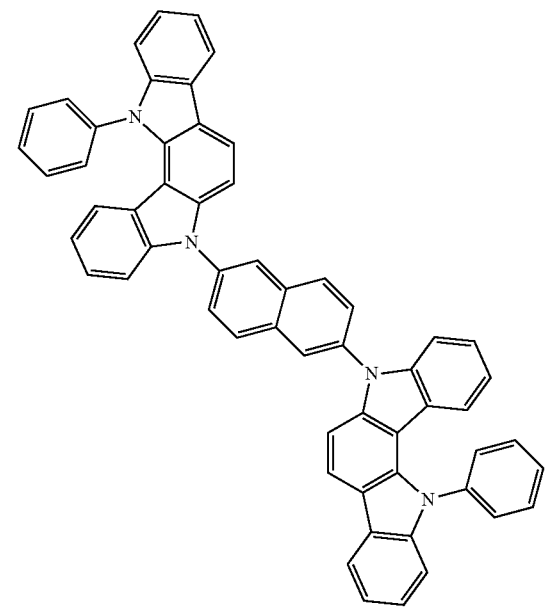
1-21
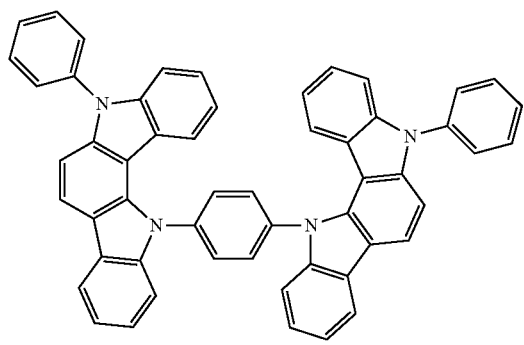
1-22
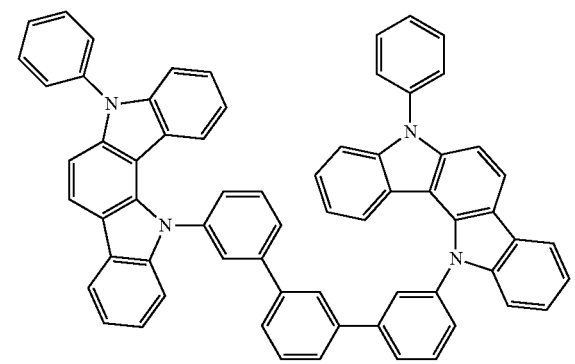

-continued
1-23
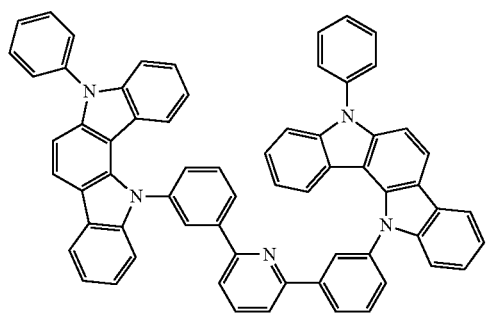
1-24
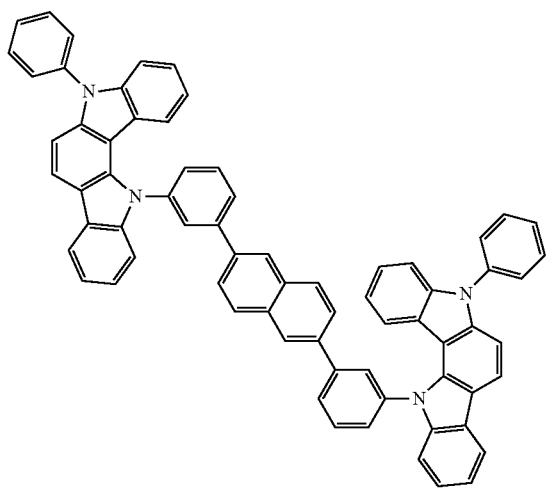
1-25
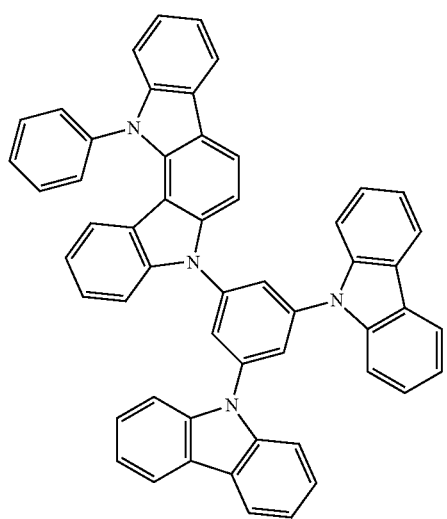
1-26
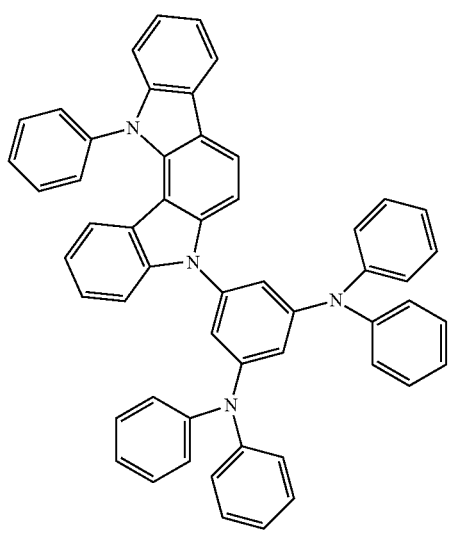
1-27
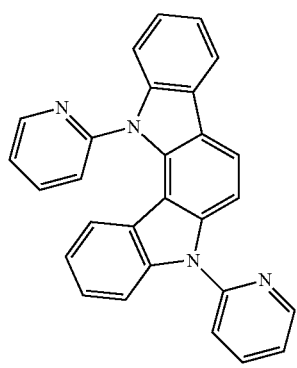
1-28
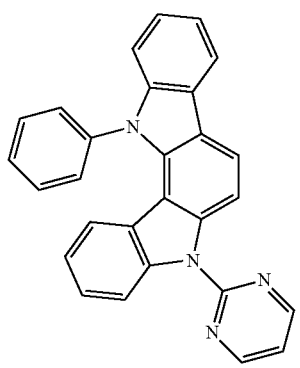

-continued
1-29
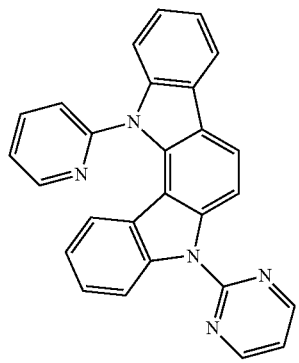
1-30
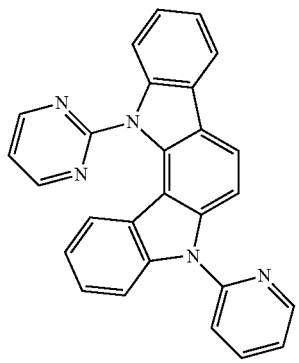
1-31
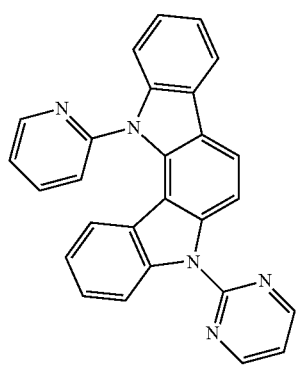
1-32
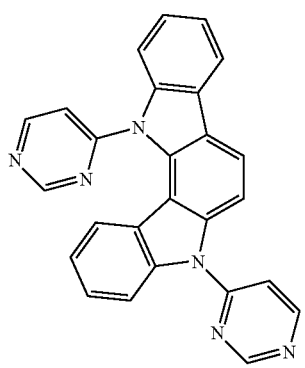
1-33
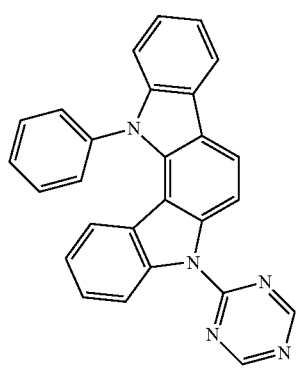
1-34
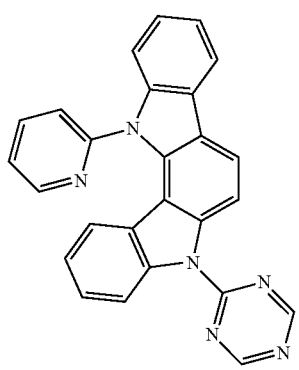
1-35
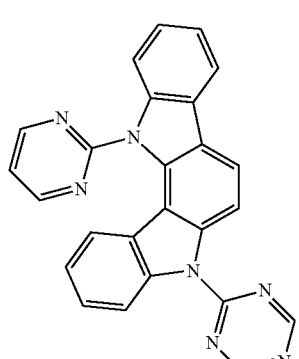
1-36
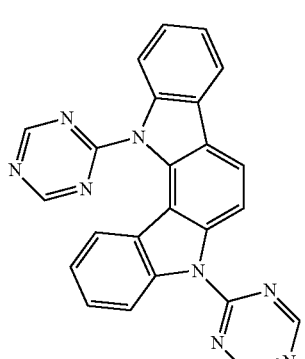

1-37
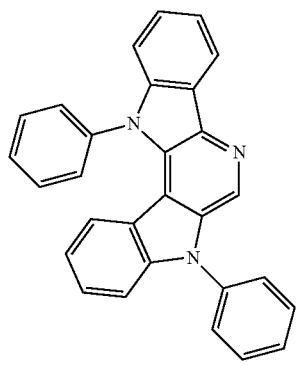
1-38
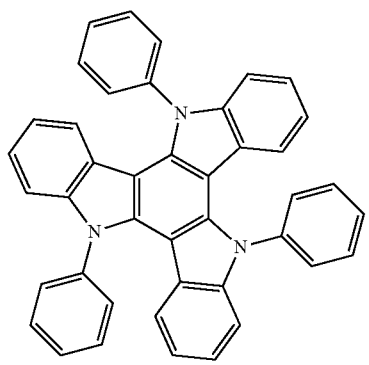
1-39
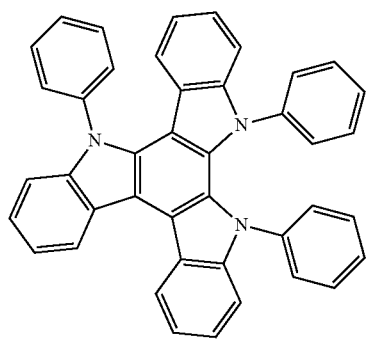
1-40
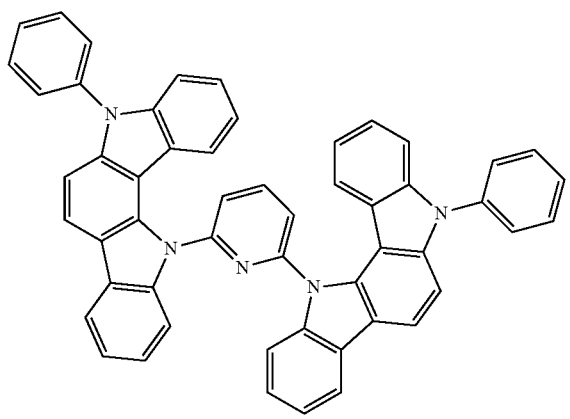
2-1
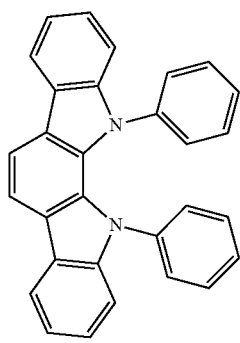
2-2
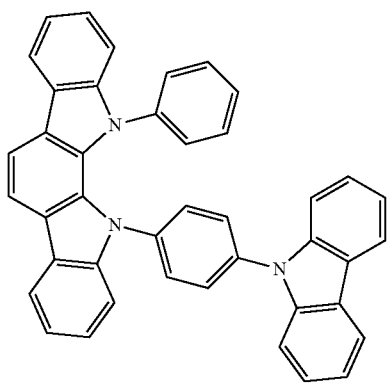

2-3
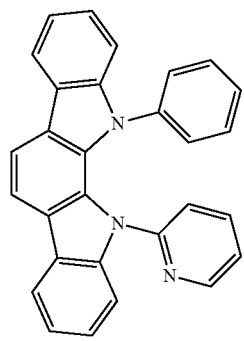
2-4
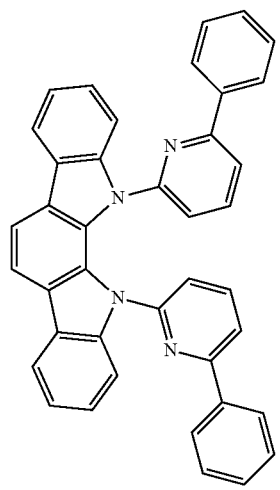
2-5
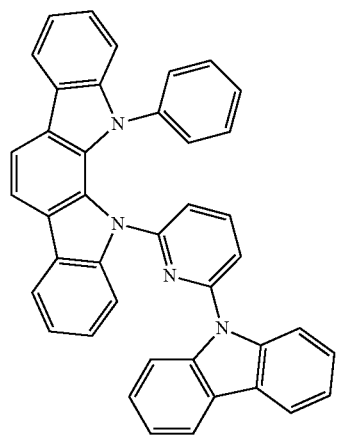
2-6
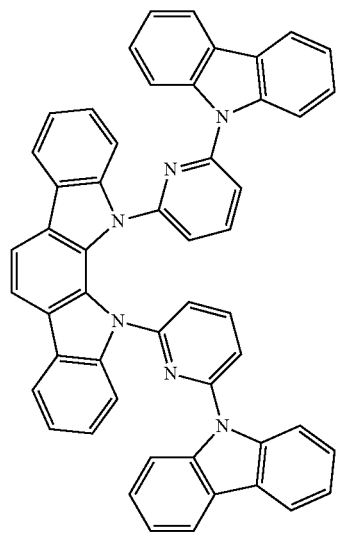
2-7
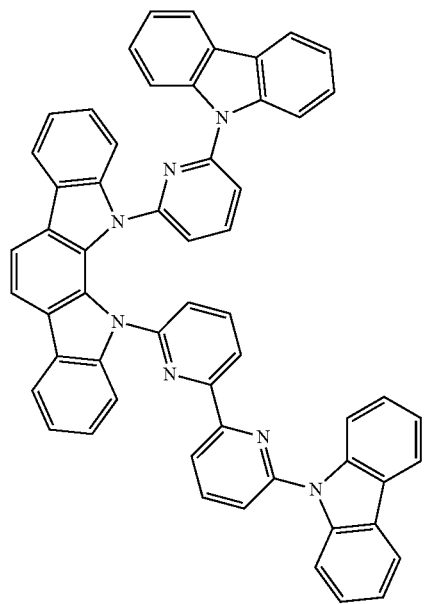
2-8
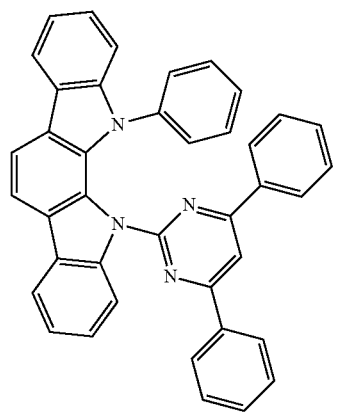

-continued
2-9
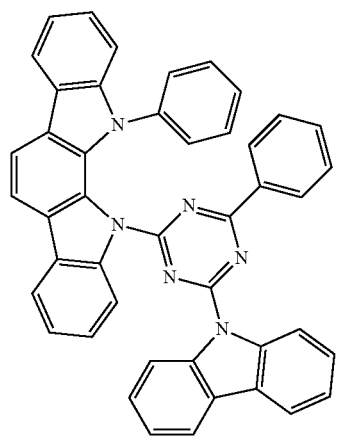
2-10
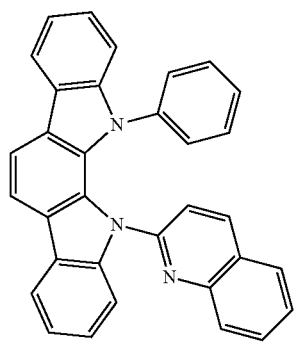
2-11
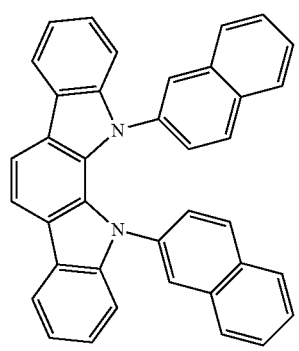
2-12
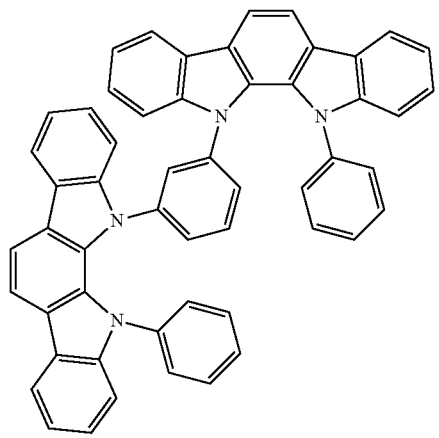
2-13
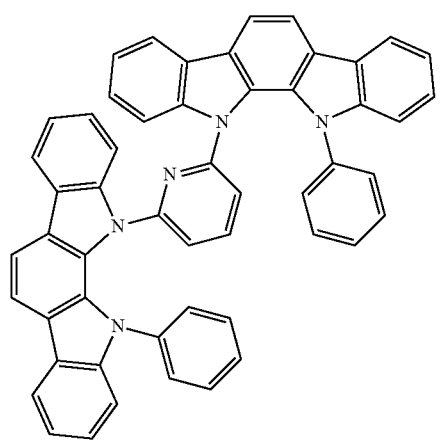
2-14
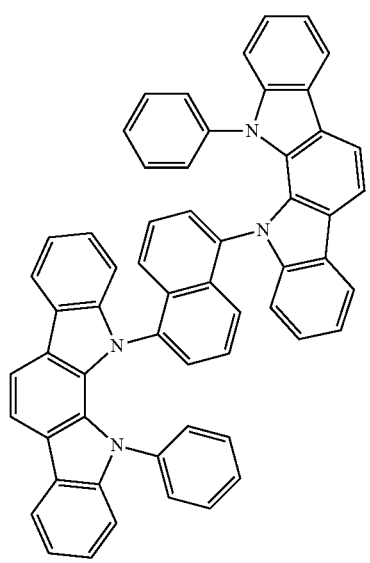

-continued
2-15
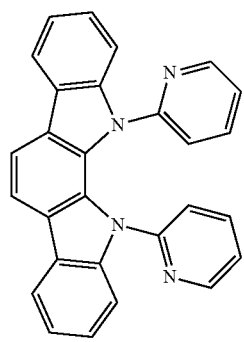
2-16
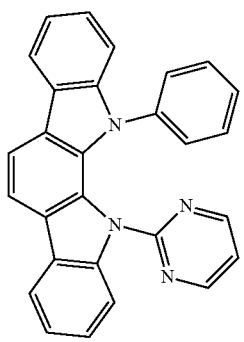
2-17
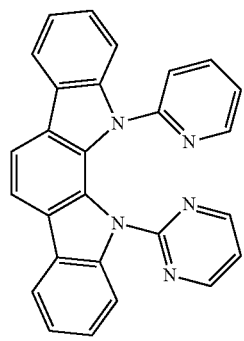
2-18
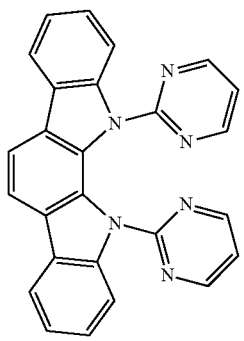
2-19
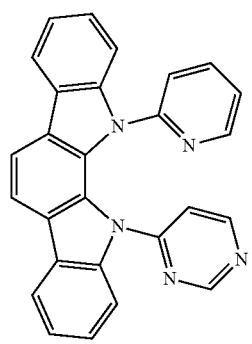
2-20
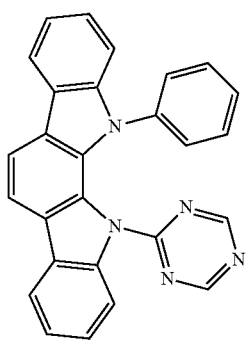
2-21
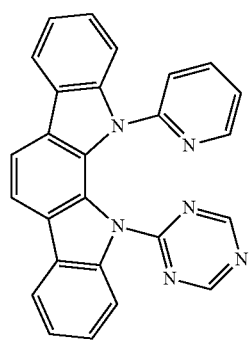
2-22
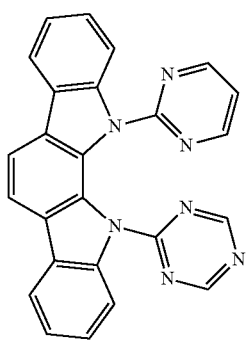

-continued
2-23
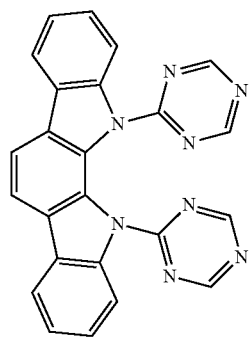
2-24
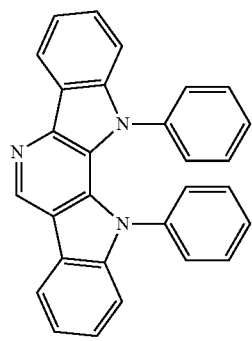
3-1
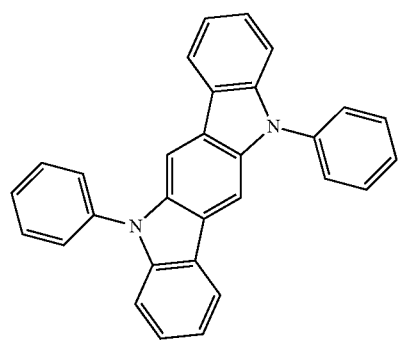
3-2
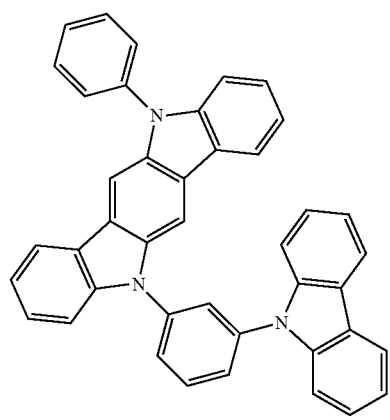
3-3
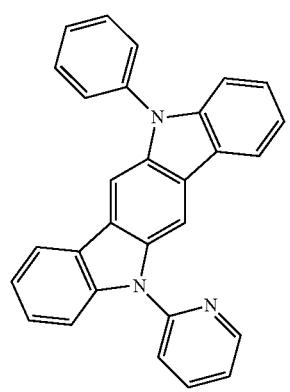
3-4
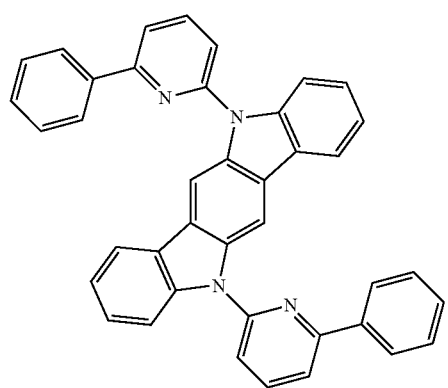
3-5
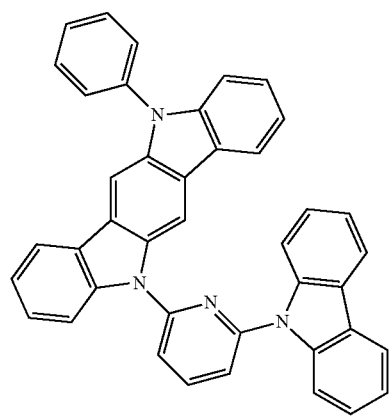
3-6
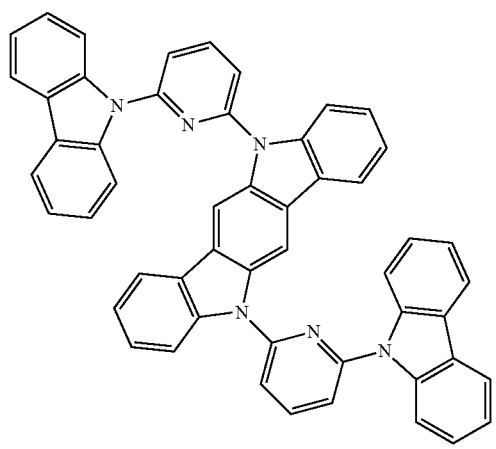

-continued
3-7
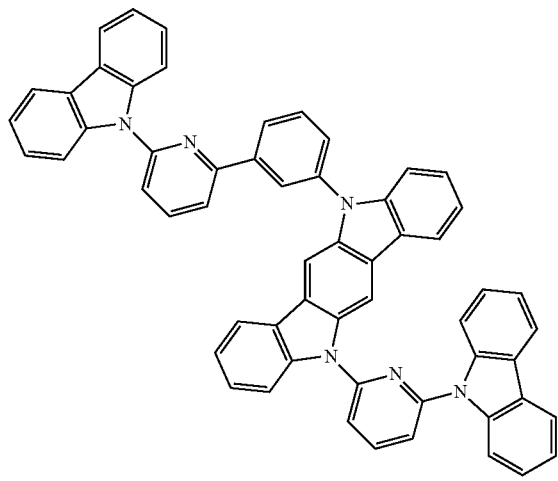
3-8
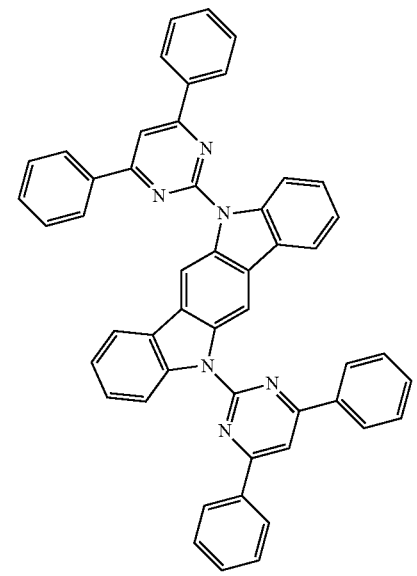
3-9
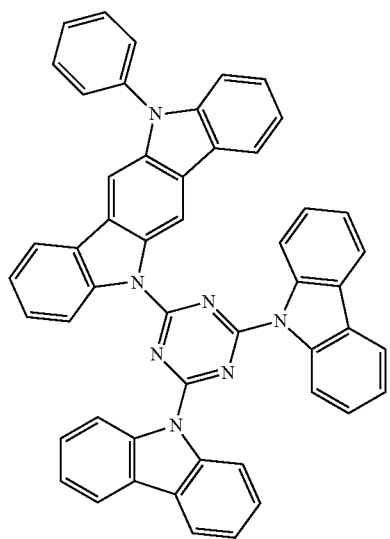
3-10
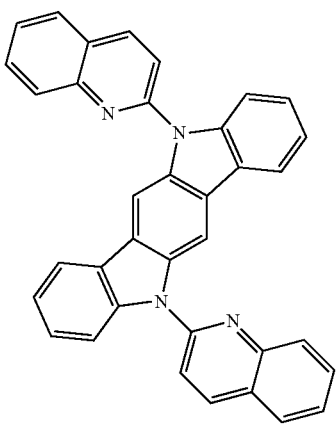
3-11
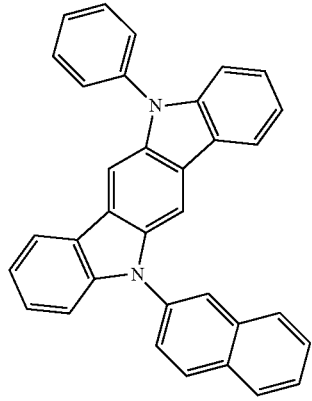
3-12
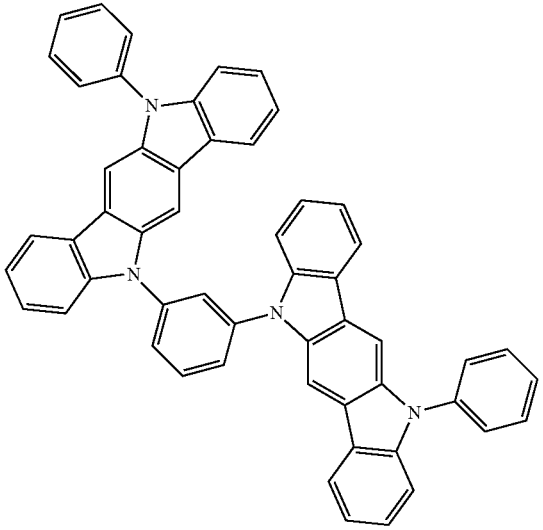

-continued
3-13
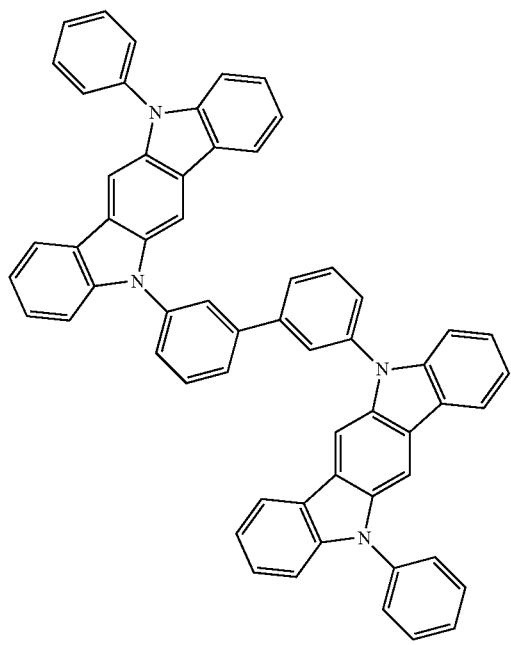
3-14
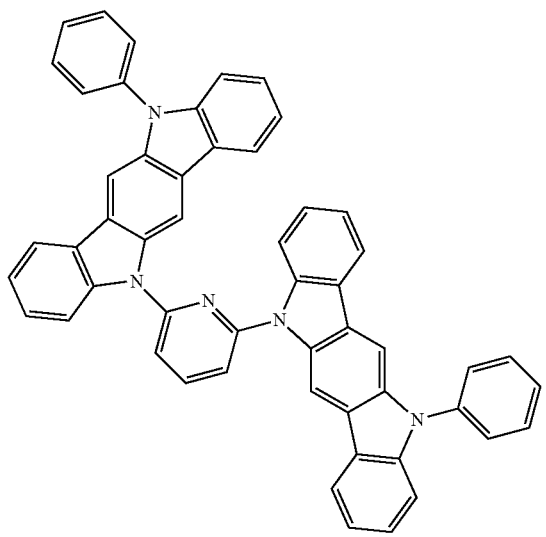
3-15
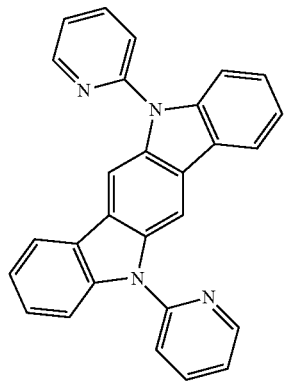
3-16
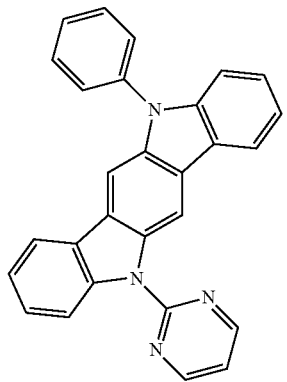
3-17
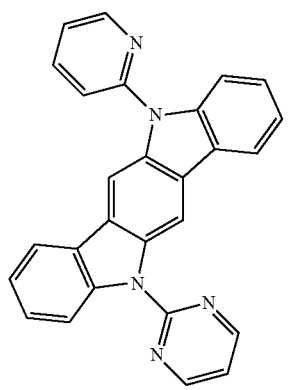
3-18
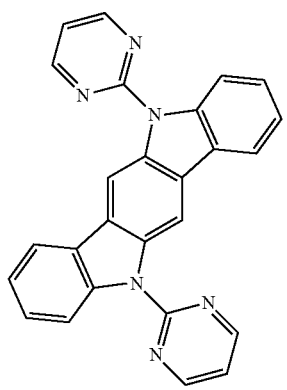

3-19
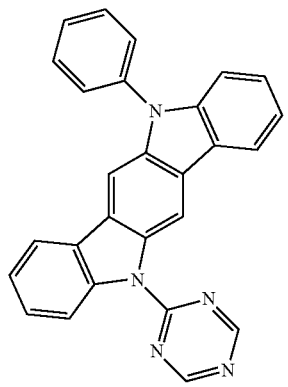
3-20
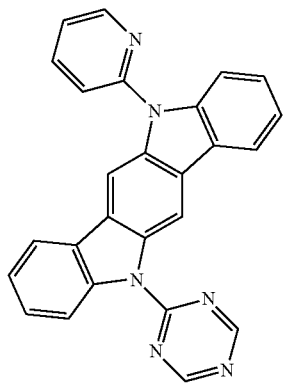
3-21
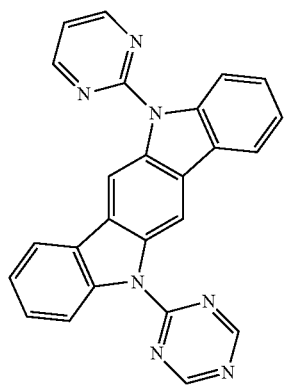
3-22
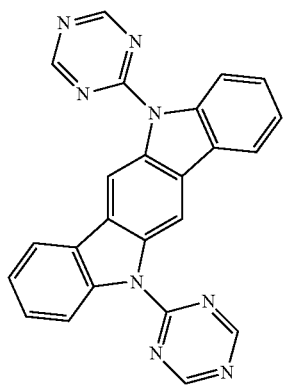
3-23
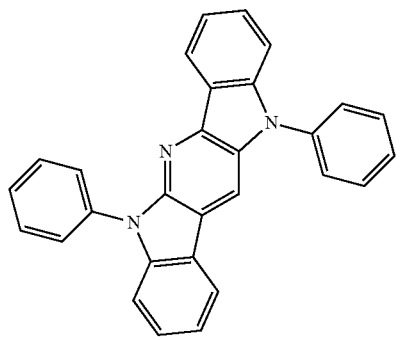
4-1
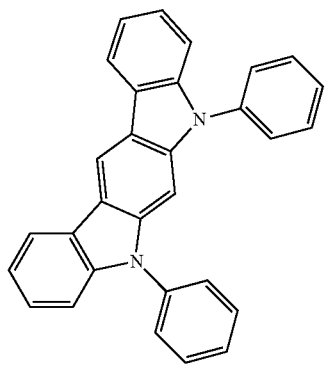
4-2
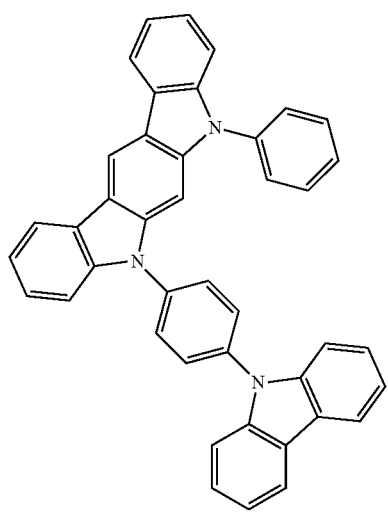
4-3
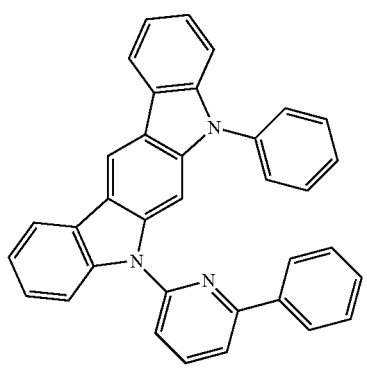

-continued
4-4
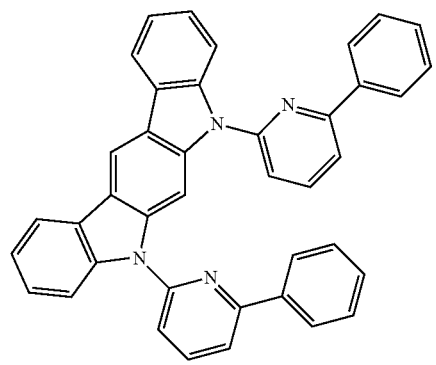
4-5
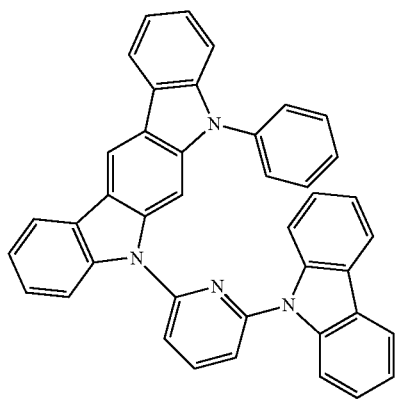
4-6
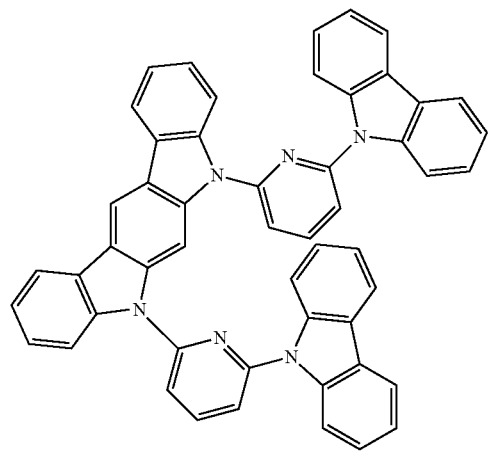
4-7
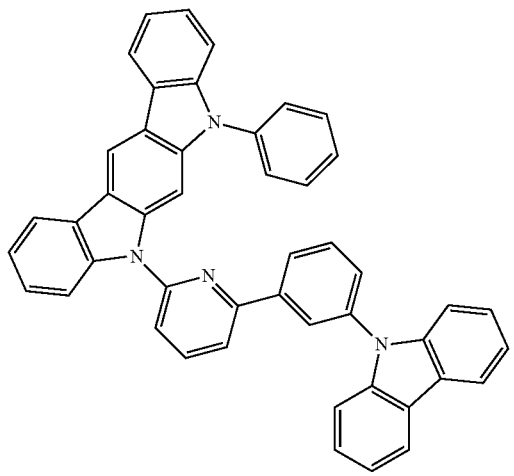
4-8
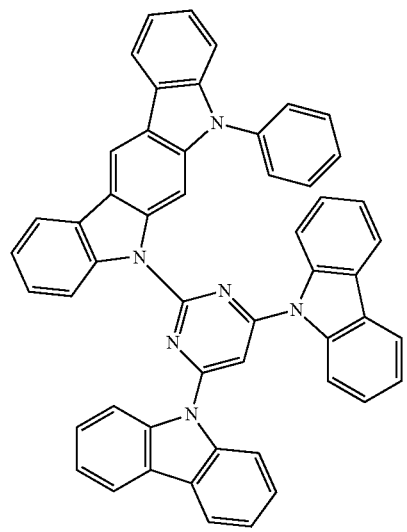
4-9
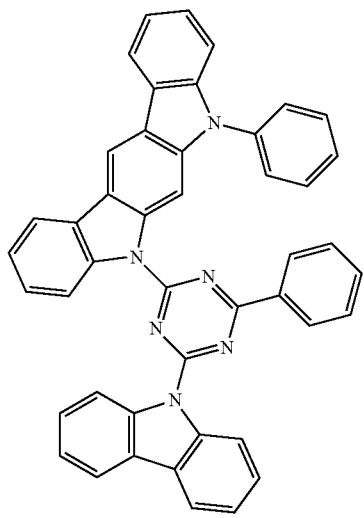

-continued
4-10
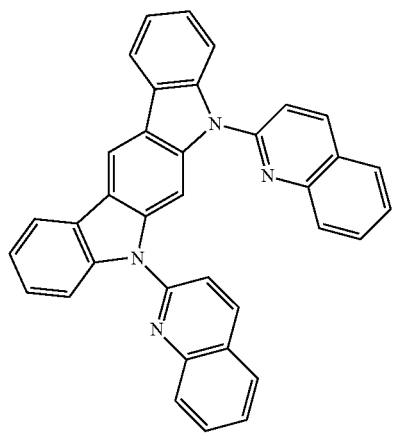
4-11
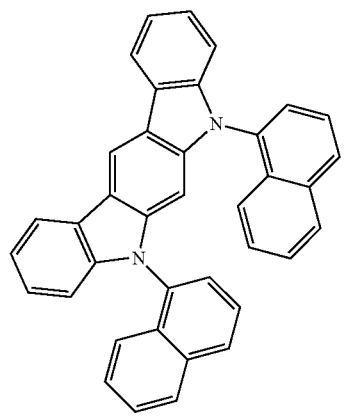
4-12
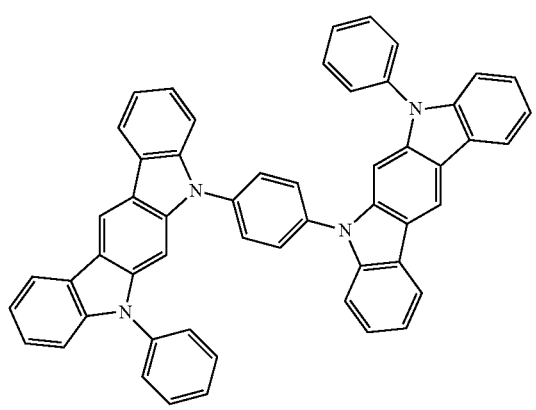
4-13
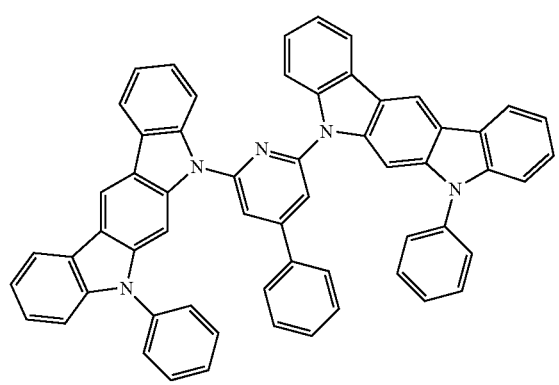
4-14
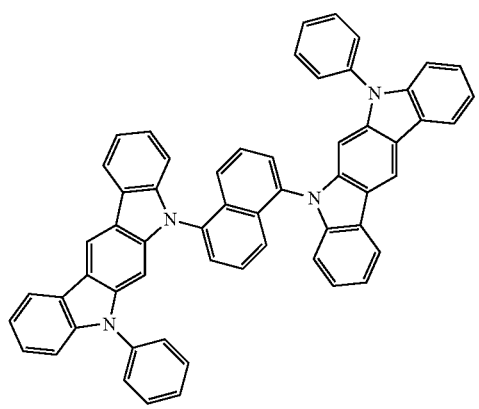
4-15
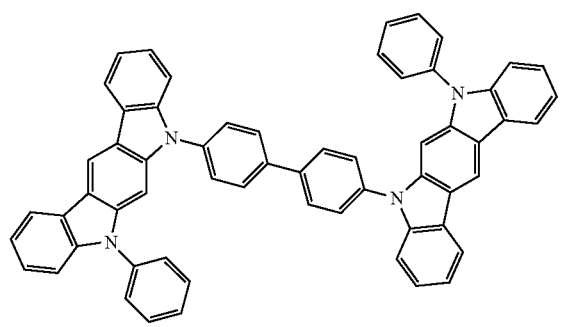

-continued
4-16
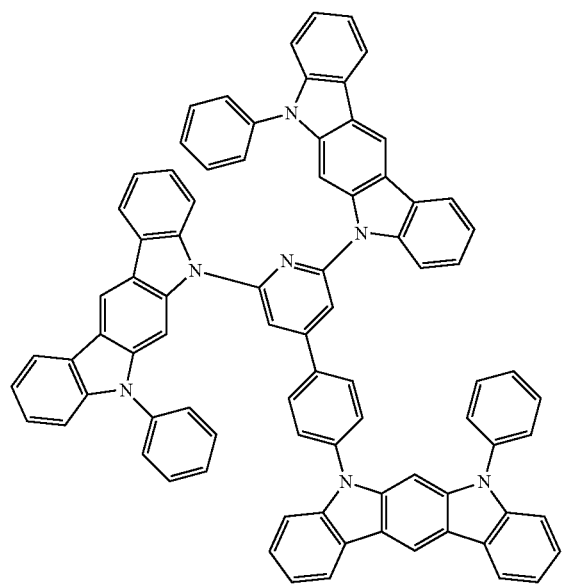
4-17
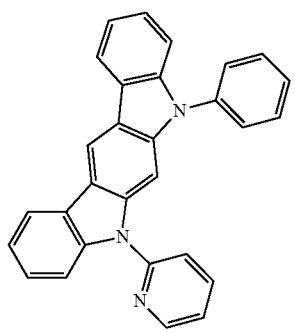
4-18
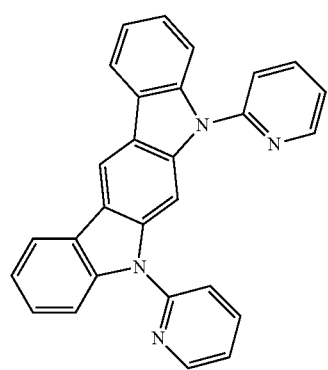
4-19
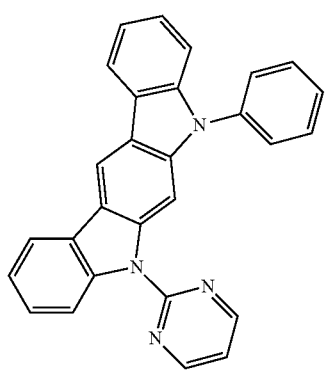
4-20
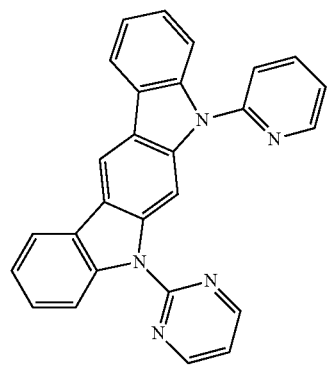
4-21
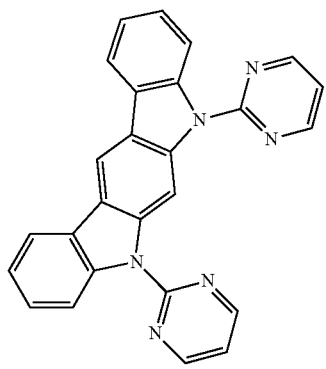

4-22
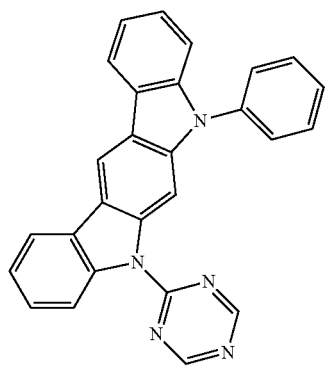
4-23
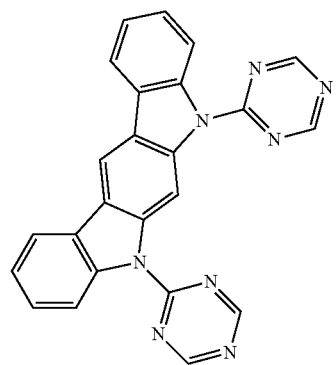
4-24
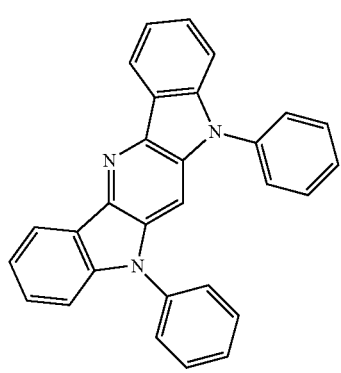
5-1
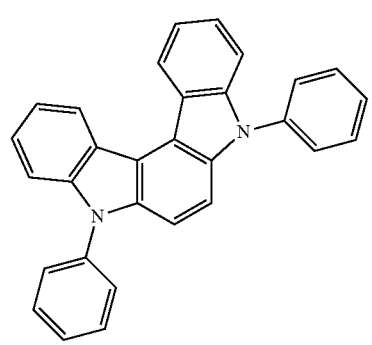
5-2
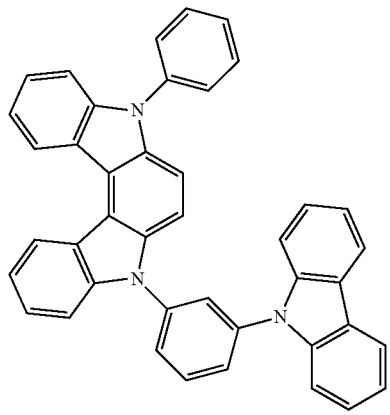
5-3
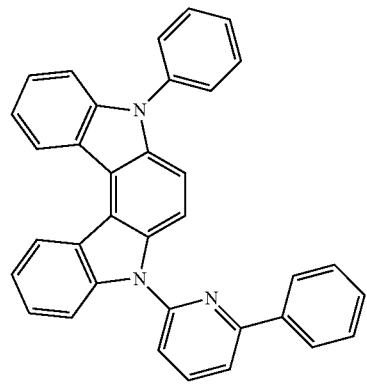
5-4
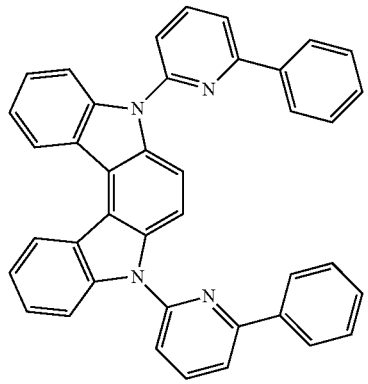
5-5
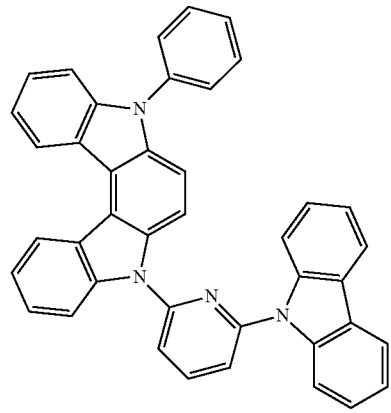

5-6
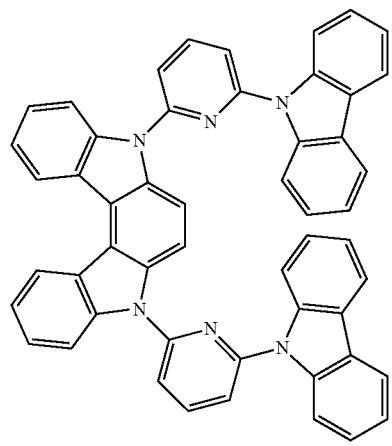
5-7
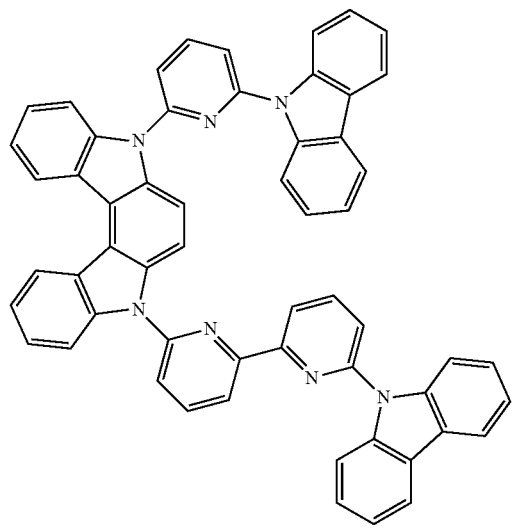
5-8
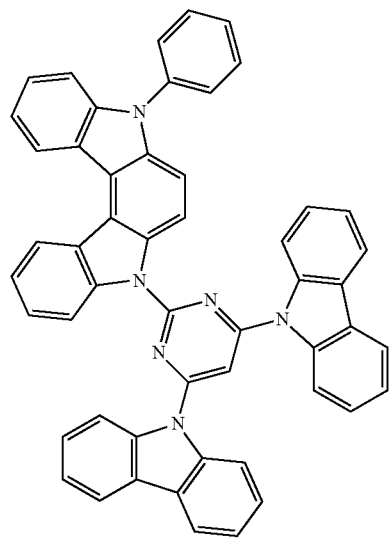
5-9
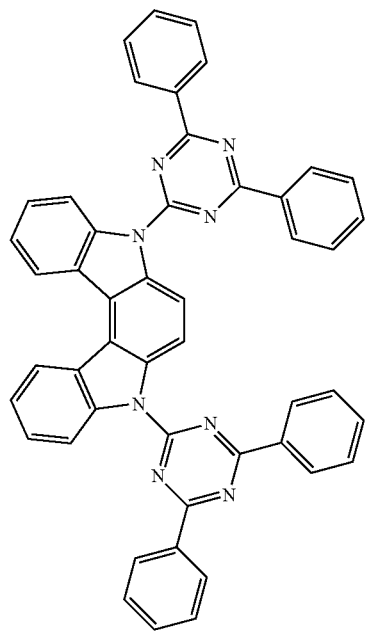
5-10
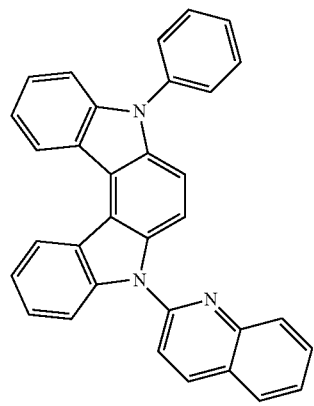
5-11
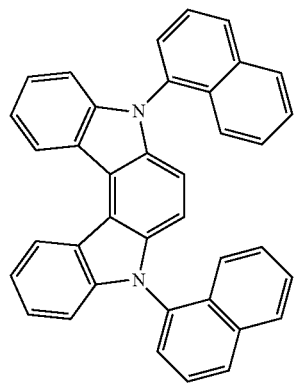

-continued
5-12
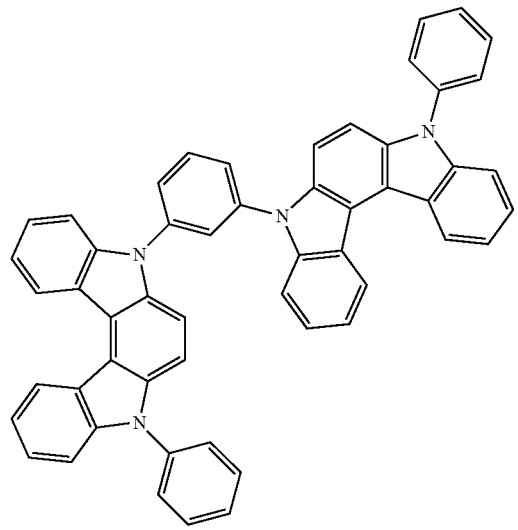
5-13
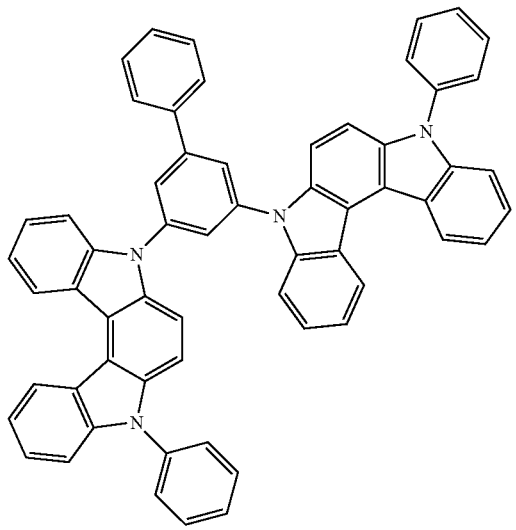
5-14
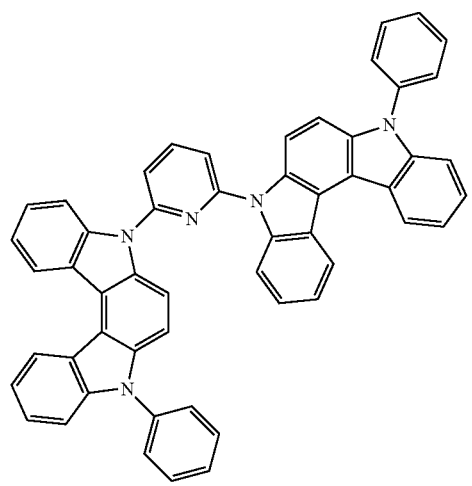
5-15
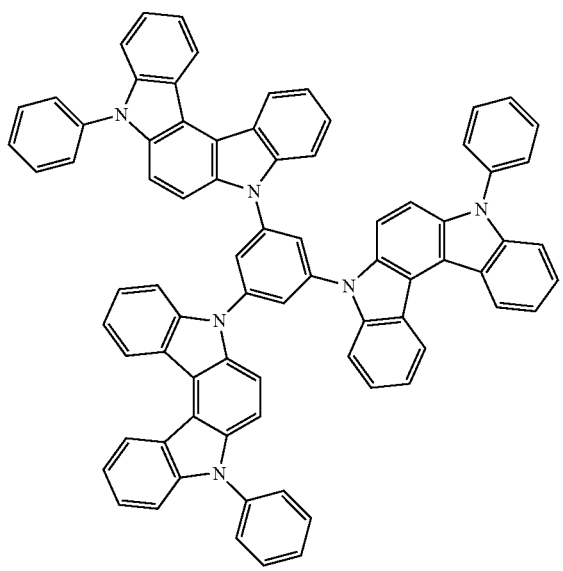
5-16
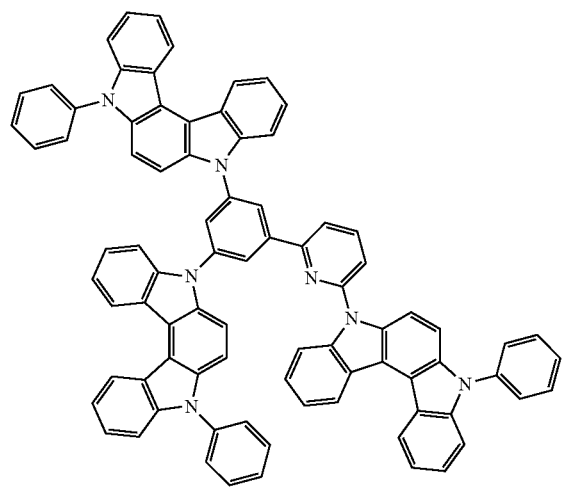
5-17
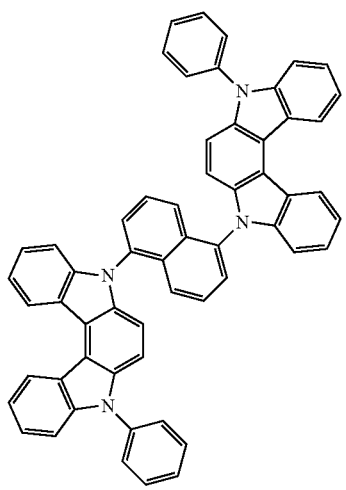

5-18
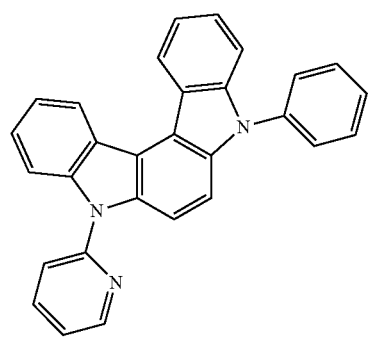
5-19
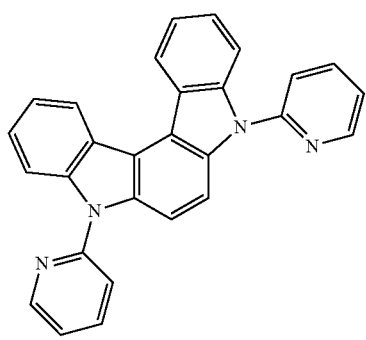
5-20
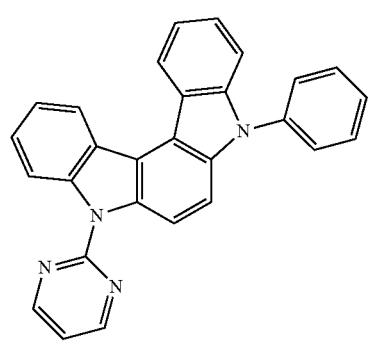
5-21
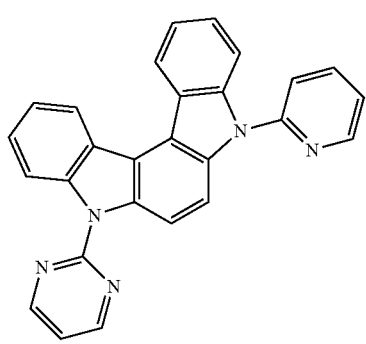
5-22
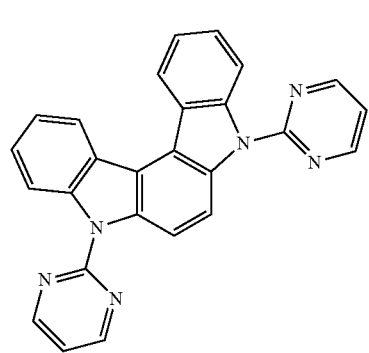
5-23
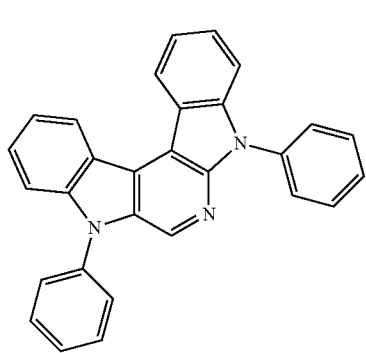
6-1
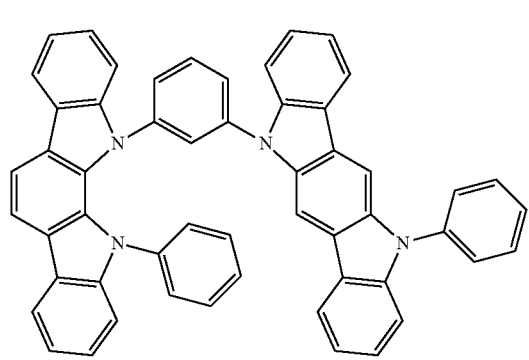
6-2
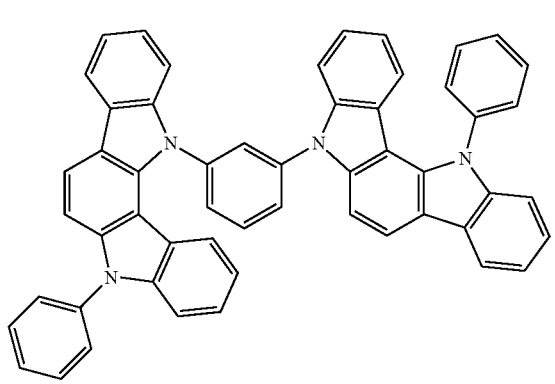

-continued
| 6-3 | 6-4 |
|---|---|
| 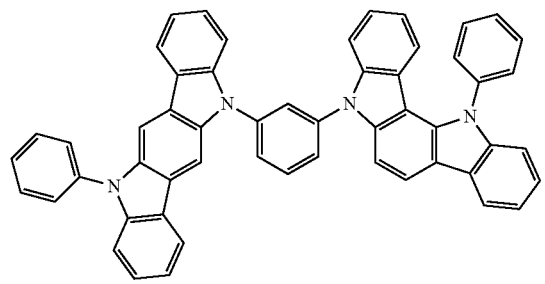 | 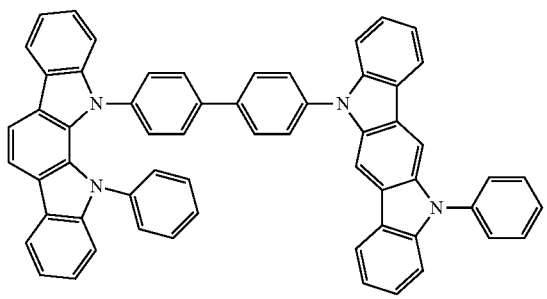 |
| 6-5 | 6-6 |
| 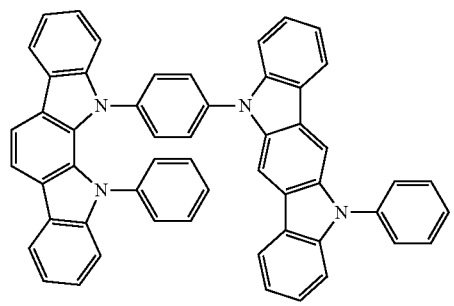 | 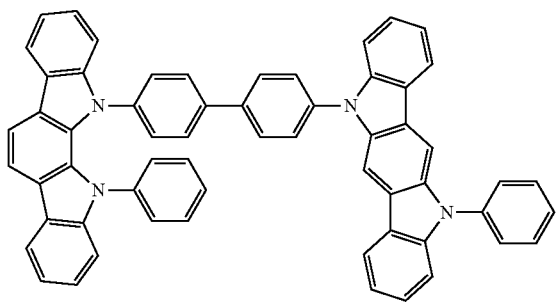 |
| 6-7 | 6-8 |
| 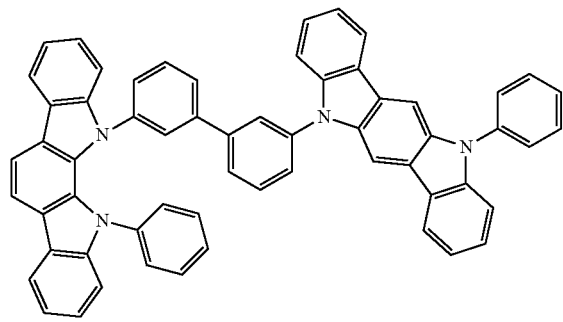 | 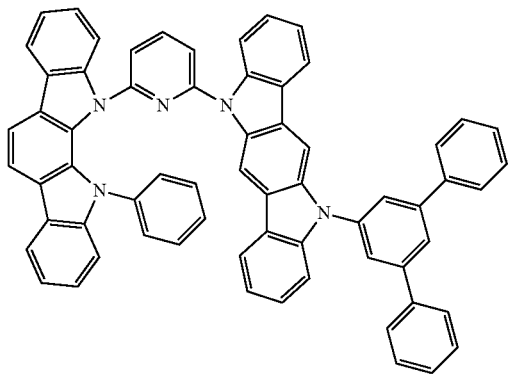 |
| 6-9 | 6-10 |
| 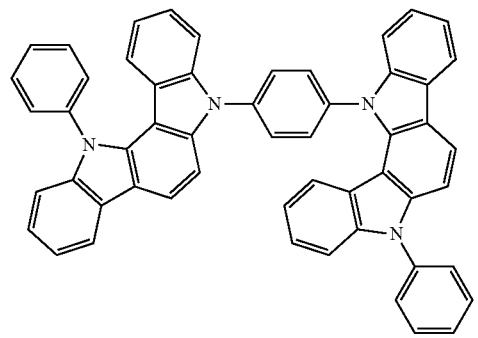 | 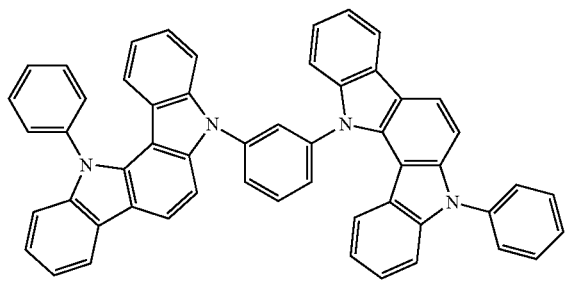 |

6-11
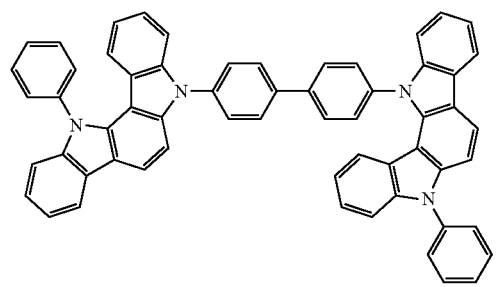
6-12
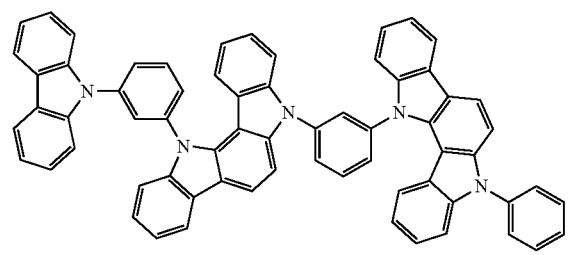
6-13
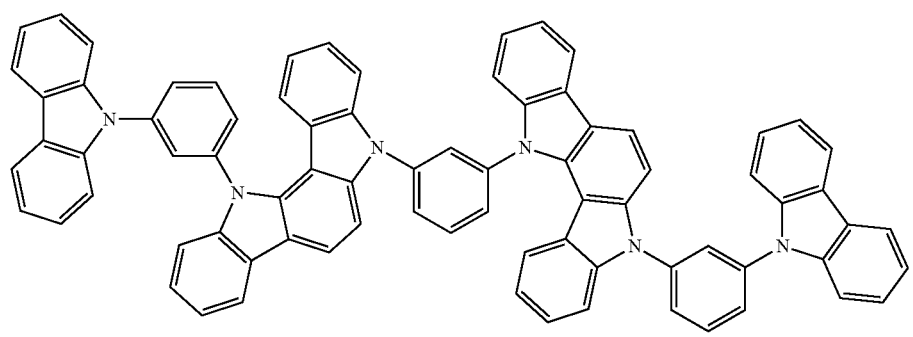
6-14
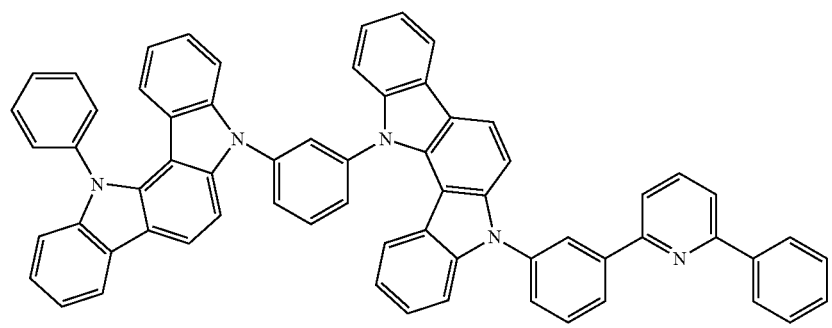
6-15
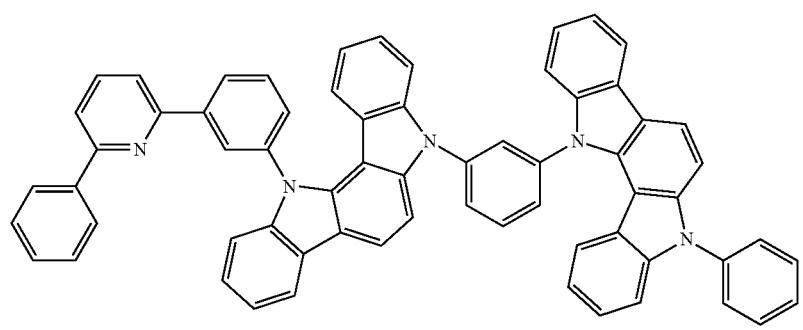

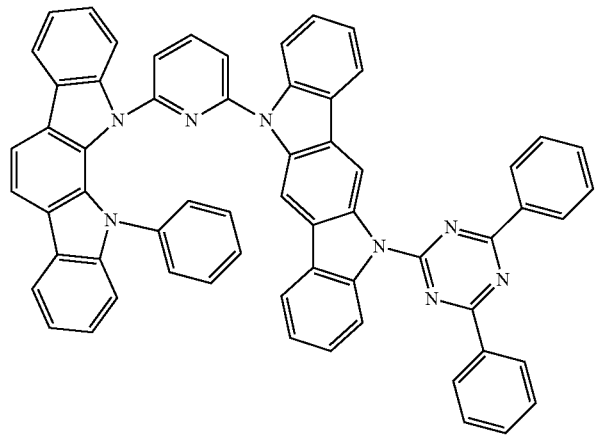

6-16

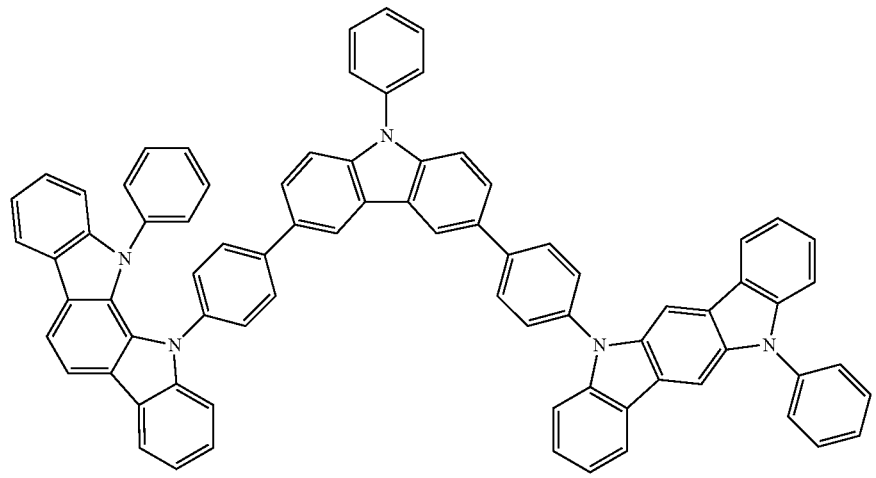

6-17

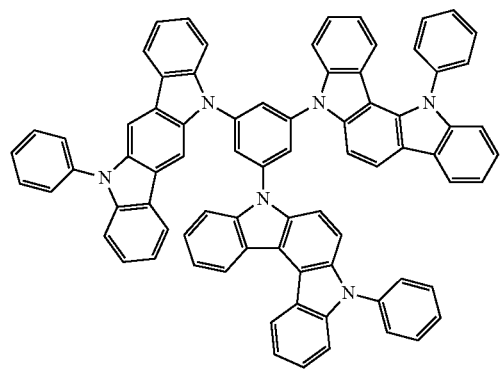

6-18

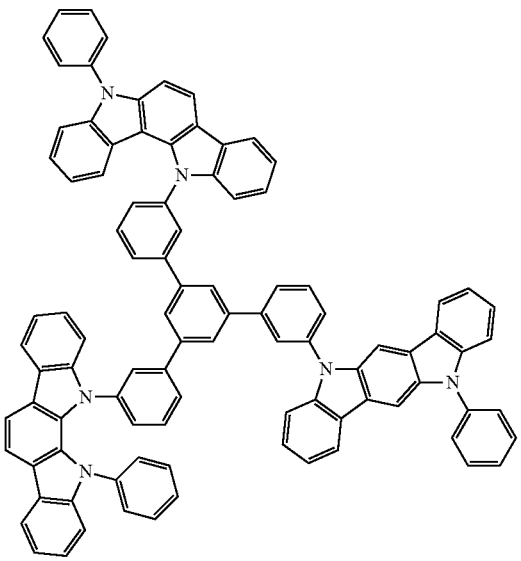

6-19

The organic EL device of this invention comprises organic layers comprising a hole-transporting layer and a light-emitting layer sandwiched between an anode and a cathode; the light-emitting layer contains a fluorescent light-emitting material; and an EB layer containing an indolocarbazole compound represented by general formula (1) is disposed between the hole-transporting layer and the light-emitting layer so as to be adjacent to the light-emitting layer.

Some of the indolocarbazole compounds represented by general formula (1) are known to be used as a hole-transporting material in the hole-transporting layer or as a host material in the light-emitting layer. According to this invention, the aforementioned EB layer is provided between the hole-transporting layer and the light-emitting layer. The material to be used in the hole-transporting layer which is provided separately from the EB layer is a hole-transporting material whose HOMO energy is higher than the HOMO energy of the indolocarbazole compound to be used in the EB layer. A hole-transporting material other than an indolocarbazole compound is preferably used.

One of the layers adjacent to the EB layer is a light-emitting layer and another is preferably a hole-transporting layer or a layer containing a hole-transporting material. Here, the layer which contains a hole-transporting material and is disposed between the EB layer and the anode functions as a hole-transporting layer as well and this layer is also referred to as hole-transporting layer in this specification. Therefore, the hole-transporting layer may be provided in one layer or in two or more layers.

The LUMO energy of the indolocarbazole compound contained in the EB layer is preferably higher than the LUMO energy of the compound contained in the adjacent light-emitting layer; or, it is higher than the LUMO energy of the main component in the case where the adjacent light-emitting layer contains a plurality of compounds. The LUMO energy of the indolocarbazole compound is higher than the LUMO energy of the compound (or the main component) contained in the light-emitting layer by 0.1 eV or more, preferably 0.3 eV or more, more preferably 0.5 eV or more.

The LUMO energy of the indolocarbazole compound is preferably −1.2 eV or more, more preferably −1.0 eV or more, most preferably −0.9 eV or more.

Furthermore, the HOMO energy of the hole-transporting material contained in the hole-transporting layer is preferably higher than the HOMO energy of the indolocarbazole compound represented by the aforementioned general formula (1). The HOMO energy of the hole-transporting material adjacent to the anode or the hole-injecting layer is preferably −4.8 eV or more, although not particularly limited thereto.

A preferable form of the organic EL device of this invention is one in which the light-emitting layer contains at least one fluorescent light-emitting material as a fluorescent dopant and at least one electron-transporting host material. In this case, electrons flowing through the light-emitting layer are efficiently blocked by the EB layer and leakage of electrons to the hole-transporting layer is reduced. This improves the probability of recombination of holes and electrons in the light-emitting layer and enhances the luminous efficiency of the fluorescent light-emitting material.

A more preferable form of the organic EL device comprises an electron-transporting layer between the cathode and the light-emitting layer in addition to the foregoing. A material to be used in the electron-transporting layer preferably has an electron mobility of $1\times10^{-7}$ cm$^2$/V·s or more, more preferably $1\times10^{-6}$ cm$^2$/V·s or more, most preferably $1\times10^{-5}$ cm$^2$/V·s or more.

The values of the LUMO energy and the HOMO energy as used in this specification are values determined by using Gaussian 03, a software for molecular orbital calculation manufactured by Gaussian, Inc. of USA, and are defined as values determined by structure optimization calculation at the B3LYP/6-31G*level.

The values of the electron mobility as used in this specification are defined as values obtained in measurements by the time of flight (TOF) method at an electric field of $E^{1/2}$=500 (V/cm)$^{1/2}$.

The structure of the organic EL device of this invention is explained below with reference to the drawing, but it will not be limited to the one illustrated in the drawing.

FIG. 1 schematically illustrates an example of the structure of an organic EL device generally used in this invention and the numbers in FIG. 1 stand for the following: 1 for a substrate, 2 for an anode, 3 for a hole-injecting layer, 4 for a hole-transporting layer, 5 for an EB layer, 6 for a light-emitting layer, 7 for an electron-transporting layer, and 8 for a cathode. The organic EL device of this invention comprises an anode, a hole-transporting layer, an EB layer, a light-emitting layer, and a cathode as essential layers; advantageously, the organic EL device comprises an anode, a hole-transporting layer, an EB layer, a light-emitting layer, an electron-transporting layer, and a cathode.

Further, the organic EL device of this invention may comprise an electron-transporting layer, an electron-injecting layer, and a hole-blocking layer in addition to the essential layers. The hole-transporting layer may be a hole-injecting/transporting layer having a hole-injecting function and the electron-transporting layer may be an electron-injecting/transporting layer having an electron-injecting function.

The organic EL device of this invention can be so constructed as to have a structure that is the reverse of the structure illustrated in FIG. 1 by piling the cathode 8, the electron-transporting layer 7, the light-emitting layer 6, the EB layer 5, the hole-transporting layer 4, and the anode 2 one upon another in this order on the substrate 1. In this case, it is also possible to add or omit a layer or layers according to the need.

The materials and the layers are respectively explained below.

—Substrate—

The organic EL device of this invention is preferably supported by a substrate. There is no specific restriction on the substrate and any of the substrates which have been used commonly in organic EL devices can be used. A substrate made from a material such as glass, transparent plastic, and quartz may be used.

—Anode—

The anode in the organic EL device is preferably made from an electrode substance having a high work function (4 eV or more) such as a metal, an alloy, an electrically conductive compound, and a mixture thereof. Specific examples of the electrode substances of this kind include metals such as Au and electrically conductive transparent materials such as CuI, indium tin oxide (ITO), SnO$_2$, and ZnO. Further, a material such as IDIXO (In$_2$O$_3$—ZnO) which is amorphous and formable into a transparent electrically conductive film may be used. The anode can be formed by preparing a thin film from any of these electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance which is applicable by coating such as an electrically conductive organic compound is used, a wet film-forming process such as printing and coating may be employed. When emitted light is taken out from the anode, the transmittance is preferably more than 10% and the sheet resistance as the anode is preferably several hundred Ω/□ or less. Further, the thickness of the film is normally in the range of 10 to 1,000 nm, preferably 10 to 200 nm, although it varies with the material used for the film.

—Cathode—

Meanwhile, the cathode is made from an electrode substance having a low work function (4 eV or less) such as a metal, an alloy, an electrically conductive compound, and a mixture thereof. Specific examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. From the viewpoint of electron-injecting property and durability against oxidation, a mixture of an electron-injecting metal and a second metal which is higher in work function and more stable than the electron-injecting metal is suitable for an electrode substance and examples include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of these electrode substances by a method such as vapor deposition and sputtering. The sheet resistance as the cathode is preferably several hundred $\Omega/\square$ or less and the thickness of the film is selected from the range of 10 nm to 5 µm, preferably 50 to 200 nm. The anode or the cathode of the organic EL device is rendered transparent or translucent in order to transmit the emitted light.

A transparent or translucent cathode may be made by using the electrically conductive transparent material described earlier in explanation of the anode and this method can be applied to the fabrication of a device in which both anode and cathode display good transmittance properties.

—Light-Emitting Layer—

The light-emitting layer is a fluorescent light-emitting layer and contains a fluorescent light-emitting material. Although at least one kind of fluorescent light-emitting material may be used singly, it is preferable that the light-emitting layer uses the fluorescent light-emitting material as a fluorescent dopant and contains a host material.

The fluorescent light-emitting materials useful for the light-emitting layer are known in a large number of patent documents and elsewhere and a suitable material can be selected from them. Examples include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, fused aromatic compounds, perinone derivatives, oxadiazole derivatives, oxazine derivatives, aldazine derivatives, pyrazyline derivatives, cyclopentadiene derivatives, bis styrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidene compounds, a variety of metal complexes represented by metal complexes of 8-quinolinol derivatives, metal complexes of pyrromethene derivatives, rare earth metal complexes, and transition metal complexes, polymer compounds such as polythiophene, polyphenylene, and polyphenylenevinylene, and organic silane derivatives. Preferable examples include fused aromatic compounds, styryl compounds, diketopyrrolopyrrole compounds, oxazine compounds, pyrromethene metal complexes, transition metal complexes, and lanthanoid complexes. More preferable examples include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]napthacene, hexacene, anthanthrene, naphtho[2,1-f]isoquinoline, α-naphthaphenanthridine, phenanthroxazole, quinolino[6,5-f]quinoline, and benzothiophanthrene. These compounds may have a substituent such as an aryl group, an aromatic heterocyclic group, a diarylamino group, and an alkyl group.

In the case where the aforementioned fluorescent light-emitting material is used as a fluorescent dopant and a host material is contained in the light-emitting layer, the content of the fluorescent dopant therein is in the range of 0.01 to 20 wt %, preferably 0.1 to 10 wt %.

The host materials useful for the light-emitting layer are known in a large number of patent documents and elsewhere and a suitable material may be selected from them. Specific examples include, but are not limited to, indole derivatives, carbazole derivatives, indolocarbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives. The aforementioned host materials are preferably compounds which are capable of preventing the wavelength of emitted light from shifting to the longer side and have a high glass transition temperature.

The host material generally has an ability to transport both holes and electrons and a material which has an excellent hole-transporting property is called a hole-transporting host material while a material which has an excellent electron-transporting property is called an electron-transporting host material.

An electron-transporting host material is preferably used in the organic EL device of this invention. The electron-transporting host material as used in this specification is defined as a host material whose electron mobility is larger than the hole mobility or defined as a host material which has an electron mobility of $1\times10^{-7}$ cm$^2$/V·s or more. An electron-transporting host material having an electron mobility of $1\times10^{-6}$ cm$^2$/V·s or more is particularly preferred.

Specific examples of the electron-transporting host materials include carbazole derivatives, indolocarbazole derivatives, pyridine, pyrimidine, triazine, imidazole derivatives, pyrazole, triazole derivatives, oxazole derivatives, oxadiazole derivatives, fluorenone derivatives, anthraquinodimethan derivatives, anthrone derivatives, diphenylquinone derivatives, thiopyran dioxide, carbodiimide, fluorenylidenemethane, distyrylpyrazine, fluorine-substituted aromatic compounds, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes containing benzoxazole or benzothiazole as a ligand.

—Injecting Layer—

The injecting layer is a layer which is provided between an electrode and an organic layer to reduce the driving voltage and improve the luminance. The injecting layer includes a hole-injecting layer and an electron-injecting layer and may be provided between the anode and the light-emitting layer or the hole-transporting layer and between the cathode and the light-emitting layer or the electron-transporting layer. The injecting layer may be provided according to the need.

—Blocking Layer—

The blocking layer is capable of blocking electric charges (electrons or holes) and/or excitons present in the light-emitting layer from diffusing to the outside of the light-emitting layer. The electron-blocking layer may be disposed between the light-emitting layer and the hole-transporting layer and blocks electrons from passing through the light-emitting layer toward the hole-transporting layer. Similarly, the hole-blocking layer may be disposed between the light-emitting layer and the electron-transporting layer and blocks holes from passing through the light-emitting layer toward the electron-transporting layer. The blocking layer may also be used to block excitons from diffusing to the outside of the light-emitting layer. That is, the electron-blocking layer and the hole-blocking layer may respectively have the function of an exciton-blocking layer. The EB layer as used in this specification means that one layer by itself has the function of an electron-blocking layer and/or an exciton-blocking layer.

—Hole-Blocking Layer—

The hole-blocking layer plays a role of blocking holes from reaching the electron-transporting layer while transporting electrons thereby improving the probability of recombination of electrons and holes in the light-emitting layer. Examples of materials for the hole-blocking layer include aluminum metal complexes, styryl derivatives, triazole derivatives, phenanthroline derivatives, oxadiazole derivatives, and boron derivatives.

—Electron-Blocking Layer—

The electron-blocking layer plays a role of blocking electrons from reaching the hole-transporting layer while transporting holes thereby improving the probability of recombination of electrons and holes in the light-emitting layer.

As a material for the electron-blocking layer, an indolocarbazole compound represented by general formula (1) is preferably used.

—Exciton-Blocking Layer—

The exciton-blocking layer is a layer for blocking excitons that are generated by the recombination of holes and electrons in the light-emitting layer from diffusing to a charge-transporting layer. The insertion of this layer enables efficient confinement of excitons in the light-emitting layer thereby enhancing the luminous efficiency of the device. The exciton-blocking layer may be inserted either on the anode side or on the cathode side or simultaneously on both anode and cathode sides so that it is adjacent to the light-emitting layer. That is, when the exciton-blocking layer is provided on the anode side, the layer may be inserted between the hole-transporting layer and the light-emitting layer so as to be adjacent to the light-emitting layer. When the exciton-blocking layer is inserted on the cathode side, the layer may be inserted between the light-emitting layer and the cathode so as to be adjacent to the light-emitting layer. Further, the hole-injecting layer, the electron-blocking layer, and the like may be provided between the anode and the exciton-blocking layer adjacent to the anode side of the light-emitting layer and the electron-injecting layer, the electron-transporting layer, the hole-blocking layer, and the like may be provided between the cathode and the exciton-blocking layer adjacent to the cathode side of the light-emitting layer.

The EB layer according to this invention functions as an electron-blocking layer and/or an exciton-blocking layer. Therefore, it is advantageous not to provide the electron-blocking layer and the exciton-blocking layer in addition to the EB layer between the light-emitting layer and the anode. It is allowable to provide the layer between the light-emitting layer and the cathode according to the need. The thickness of the EB layer is preferably 3 to 100 nm, more preferably 5 to 30 nm.

As a material for the exciton-blocking layer, the indolocarbazole compound represented by general formula (1) is preferably used and this compound is more preferably used in the exciton-blocking layer on the anode side. Other known exciton-blocking materials may be used as well.

The materials which are known as useful for the exciton-blocking layer include 1,3-dicarbazolylbenzene (mCP) and bis(2-methyl-8-quinolinolato)-4-phenylphenolatoaluminum (III) (BAlq).

—Hole-Transporting Layer—

The hole-transporting layer is made from a hole-transporting material which has a function of transporting holes and it may be provided in a single layer or a plurality of layers. The hole-transporting layer is disposed between the EB layer and the anode and contains a hole-transporting material. The hole-transporting layer is preferably provided adjacent to the anode or the hole-injecting layer.

The hole-transporting material has a function of transporting holes and may have a function of injecting holes as well. The hole-transporting material may be an organic material or an inorganic material. Examples of known useful hole-transporting materials include triazole derivatives, oxadiazole derivatives, imidazole derivatives, carbazole derivatives, indolocarbazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Preferable examples include porphyrin compounds, aromatic tertiary amine compounds, and styrylamine compounds and more preferable examples include aromatic tertiary amine compounds.

The indolocarbazole compound contained in the EB layer is also one kind of hole-transporting material. When a layer containing this compound is arranged on the side of the light-emitting layer separately from the hole-transporting layer, the layer functions as an EB layer.

Although organic EL devices using two or more hole-transporting layers are known, an example of arranging and using an indolocarbazole compound at the same position as that of the EB layer in the organic EL device of this invention is not known. The arrangement of the aforementioned EB layer produces an incomparably remarkable effect. It is plausible that the EB layer which produces such a remarkable effect has a high LUMO energy to display an excellent electron-blocking effect and an appropriate HOMO energy and an adequate hole-transporting ability to prevent leakage of electrons and excitons from the light-emitting layer, thereby providing stable and good device characteristics. Even though a large number of hole-transporting materials have been known, no compound suitable for use in an EB layer to provide the aforementioned good device characteristics has been known until it has been found by the inventors of this invention for the first time. In the case where the aforementioned indolocarbazole compound is incorporated in an ordinary hole-transporting layer and this particular hole-transporting layer is a single layer, the HOMO energy does not match and, as a result, the driving voltage tends to rise to a higher level and the life tends to become shorter.

—Electron-Transporting Layer—

The electron-transporting layer is formed from a material which has a function of transporting electrons and may be provided in a single layer or a plurality of layers.

An electron-transporting material may be an arbitrary material so long as it has a function of transporting electrons which are injected from the cathode to the light-emitting layer. A material applicable to the electron-transporting layer is exemplified by an aluminum complex typified by Alq3, a nitro-substituted fluorene derivative, a diphenylquinone derivative, a thiopyran dioxide derivative, carbodimide, a fluorenylidenemethane derivative, an anthraquinodimethan derivative, an anthrone derivative, and an oxadiazole derivative. Further, a thiadiazole derivative which is derived from the aforementioned oxadiazole derivative by substituting a sulfur atom for the oxygen atom of an oxadiazole ring and a quinoxaline derivative having a quinoxaline ring which is known as an electron-withdrawing group may be used as an electron-transporting material. Further, a phosphorus-containing derivative and a silicon-containing derivative have high electron mobilities and are preferable electron-transporting materials. Still further, a polymer material which contains any of these materials in the polymer chain or a polymer material whose backbone is constituted of any of these materials may be used.

—EB Layer—

The EB layer is a layer which has a function of the electron-blocking layer and/or the exciton-blocking layer and contains an indolocarbazole compound represented by general formula (1).

The organic EL device of this invention may be any of a single device, a device having a structure arranged in array, and a device in which the anode and the cathode are arranged in X-Y matrix. The provision of the EB layer between the hole-transporting layer and the fluorescent light-emitting layer so as to be adjacent to the light-emitting layer enables the organic EL device of this invention to block electrons and/or excitons from leaking from the light-emitting layer to the hole-transporting layer. Thus, a device which is improved markedly in luminous efficiency and driving stability compared to a conventional device is obtained.

EXAMPLES

This invention is explained in more detail hereinafter with reference to the examples. However, this invention is not limited to the examples and can be reduced to practice in various modes unless such a practice exceeds the gist of this invention.

Synthetic examples of the compounds of this invention are hereinafter described. The compound numbers correspond to the numbers given to the aforementioned chemical formulas.

Synthetic Example 1

Synthesis of Compound 1-1

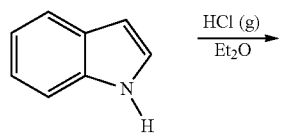

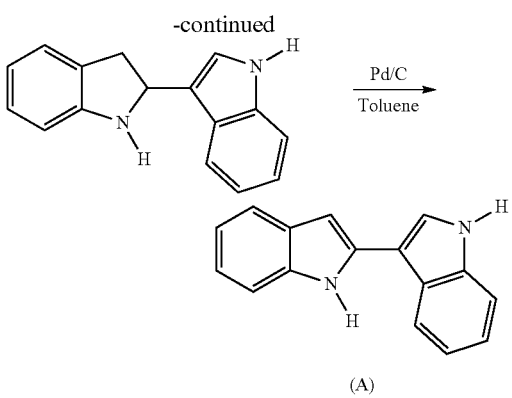

(A)

Under a nitrogen atmosphere, a hydrogen chloride gas generated by adding dropwise 112.0 g (1.10 mol) of concentrated hydrochloric acid to 211.7 g (2.16 mol) of concentrated sulfuric acid over 1 hour was blown into a solution of 20.0 g (0.17 mol) of indole in 300 ml of dehydrated diethyl ether with stirring at room temperature. The reaction solution was stirred at room temperature for 15 hours and, thereafter, 121.0 g of ethyl acetate and 303.2 g of a saturated aqueous sodium hydrogen carbonate solution were added. The aqueous layer was extracted with ethyl acetate (2×100 ml) and then the organic layer was washed with a saturated aqueous sodium hydrogen carbonate solution (100 ml) and distilled water (2×100 ml). The organic layer was dried over anhydrous magnesium sulfate, the magnesium sulfate was separated by filtration, and the solvent was distilled off under reduced pressure. The residue was dissolved in 150 ml of toluene, 2.5 g of palladium/activated carbon was added, and the mixture was heated under reflux at 111° C. with stirring for 3 hours. The reaction solution was cooled to room temperature, the palladium/activated carbon was separated by filtration, and the solvent was distilled off under reduced pressure. The residue was purified by recrystallization to give 14.7 g (37% yield) of Intermediate A as a white crystal.

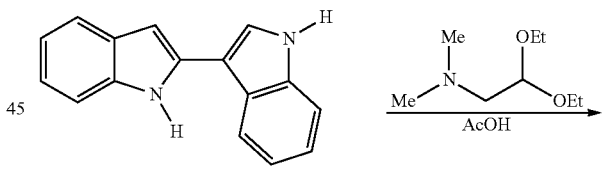

(A)

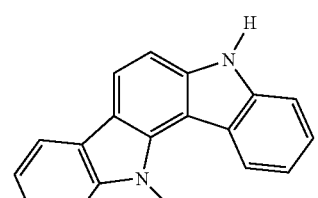

(B)

Under a nitrogen atmosphere, 14.1 g (0.061 mol) of Intermediate A, 11.4 g (0.071 mol) of N,N-dimethylaminoacetaldehyde diethyl acetal, and 110.0 g of acetic acid were heated under reflux at 118° C. with stirring for 8 hours. The reaction solution was cooled to room temperature and the precipitated crystal was collected by filtration and washed with acetic acid (30 ml). The crystal thus obtained was purified by reslurrying to give 10.4 g (67% yield) of Intermediate B as a white crystal.

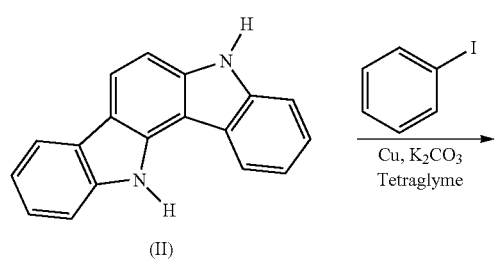

(II)

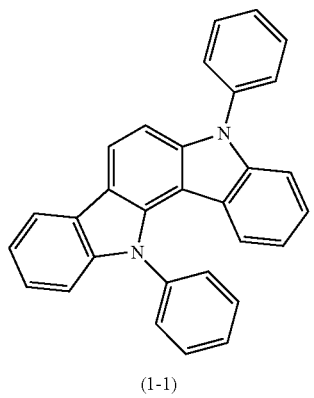

(1-1)

Figure 2:
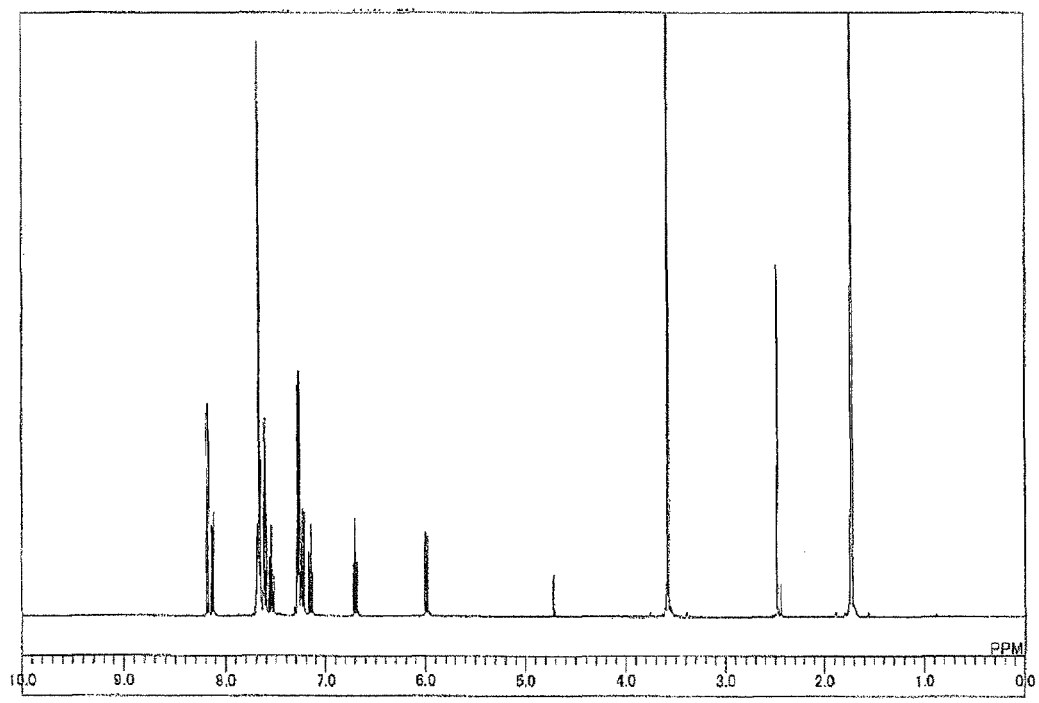
FIG. 2 shows a $^1$H-NMR chart of Compound 1-1.

Under a nitrogen atmosphere, 10.0 g (0.039 mol) of Intermediate B, 79.6 g (0.39 mol) of iodobenzene, 12.4 g (0.20 mol) of copper, 16.2 g (0.12 mol) of potassium carbonate, and 200 ml of tetraglyme were heated at 190° C. with stirring for 72 hours. The reaction solution was cooled to room temperature and an inorganic matter was separated by filtration. To the remaining solution was added distilled water (200 ml) with stirring and the precipitated crystal was collected by filtration. The crystal was purified by silica gel column chromatography to give 10.0 g (65% yield) of Compound 1-1 as a white solid. APCI-TOFMS: m/z 409 [M+H]⁺. The results of ¹H-NMR measurement (solvent: THF-d8) are shown in FIG. 2.

Synthetic Example 2

Synthesis of Compound 2-1

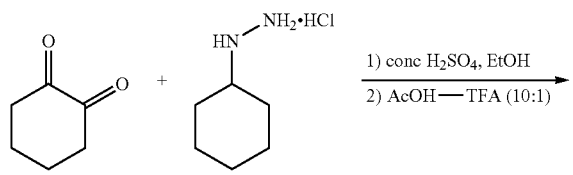

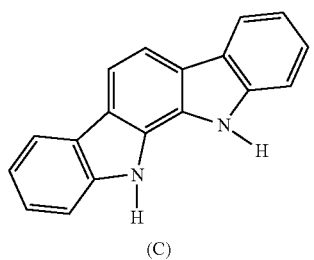

(C)

Under a nitrogen atmosphere, 3.0 g (0.031 mol) of concentrated sulfuric acid was added dropwise over 5 minutes to 33.3 g (0.30 mol) of 1,2-cyclohexanedione, 86.0 g (0.60 mol) of phenylhydrazine hydrochloride, and 1,000 ml of ethanol with stirring at room temperature and then the resulting mixture was heated at 65° C. with stirring for 4 hours. The reaction solution was cooled to room temperature and the precipitated crystal was collected by filtration and washed with ethanol (2×500 ml) to give 80.0 g of a purplish brown crystal. This crystal, weighing 72.0 g (0.26 mol), was heated together with 72.0 g of trifluoroacetic acid and 720.0 g of acetic acid at 100° C. with stirring for 15 hours. The reaction solution was cooled to room temperature and the precipitated crystal was collected by filtration, washed with acetic acid (200 ml), and purified by reslurrying to give 30.0 g (45% yield) of Intermediate C as a white crystal.

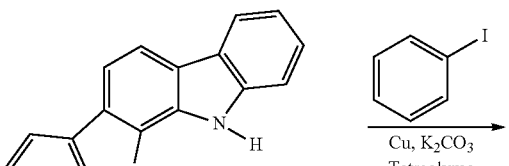

(C)

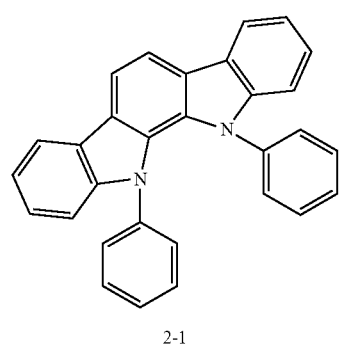

2-1

Figure 3:
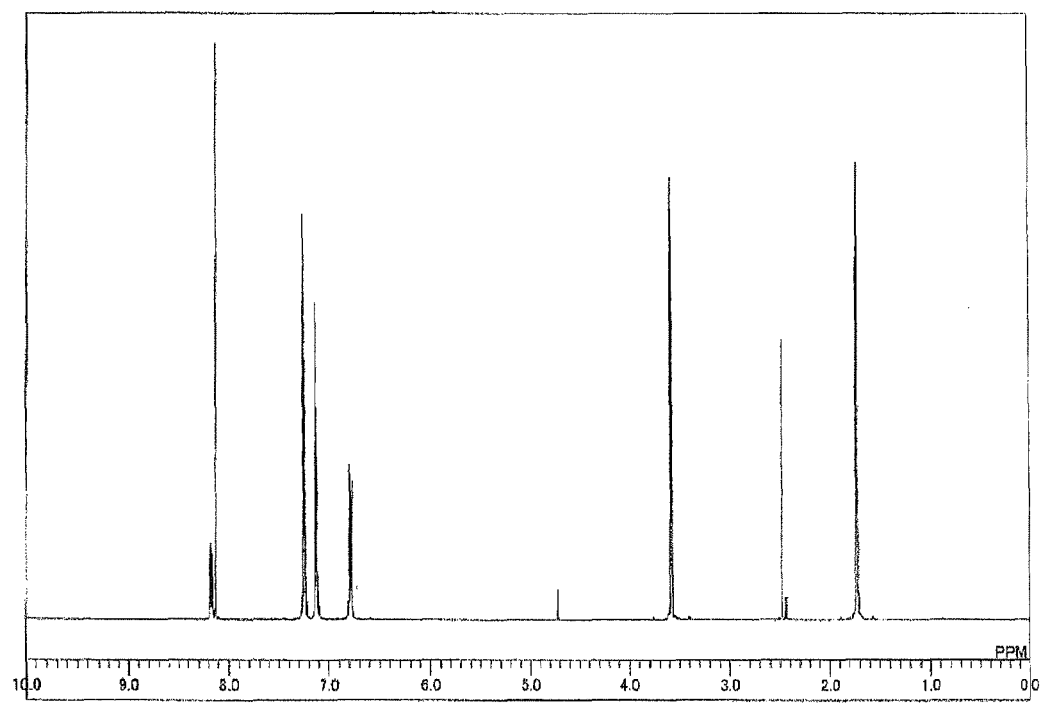
FIG. 3 shows a $^1$H-NMR chart of Compound 2-1.

Under a nitrogen atmosphere, 10.0 g (0.039 mol) of Intermediate C, 79.6 g (0.39 mol) of iodobenzene, 12.4 g (0.20 mol) of copper, 21.6 g (0.16 mol) of potassium carbonate, and 200 ml of tetraglyme were heated at 190° C. with stirring for 120 hours. The reaction solution was cooled to room temperature and an inorganic matter was separated by filtration. To the remaining solution was added distilled water (200 ml) with stirring and the precipitated crystal was collected by filtration and purified by silica gel column chromatography to give 9.6 g (60% yield) of Compound 2-1 as a white solid. APCI-TOFMS: m/z 409 [M+H]⁺. The results of ¹H-NMR measurement (solvent: THF-d8) are shown in FIG. 3.

Synthetic Example 3

Synthesis of Compound 3-1

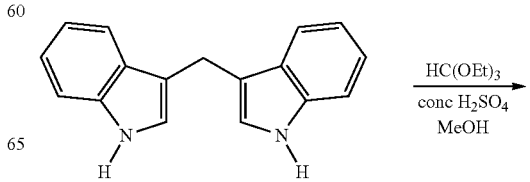

-continued

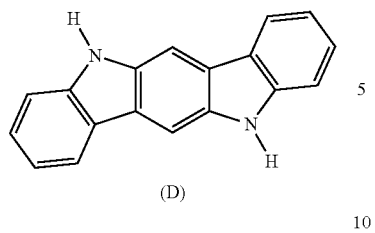
(D)

Under a nitrogen atmosphere, 5.0 g (0.052 mol) of concentrated sulfuric acid was added dropwise over 3 minutes to 50.69 g (0.21 mol) of 3,3'-methylenediindole, 30.55 g (0.21 mol) of triethyl orthoformate, and 640 g of methanol with stirring at room temperature. The mixture was then heated under reflux at 65° C. with stirring for 1 hour. The reaction solution was cooled to room temperature and the precipitated crystal was collected by filtration and washed with methanol to give 36.81 g (70% yield) of Intermediate D as a reddish brown crystal.

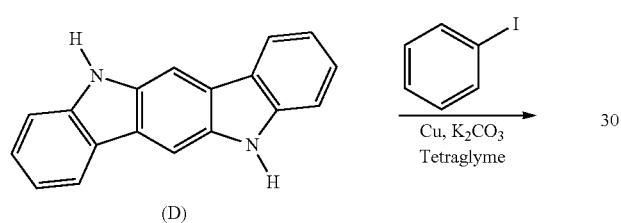

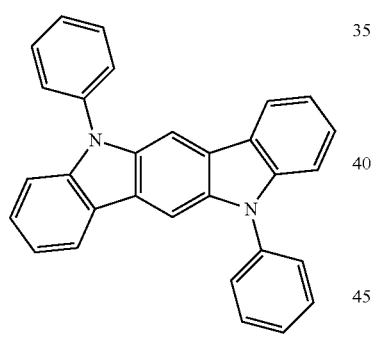

3-1

Figure 4:
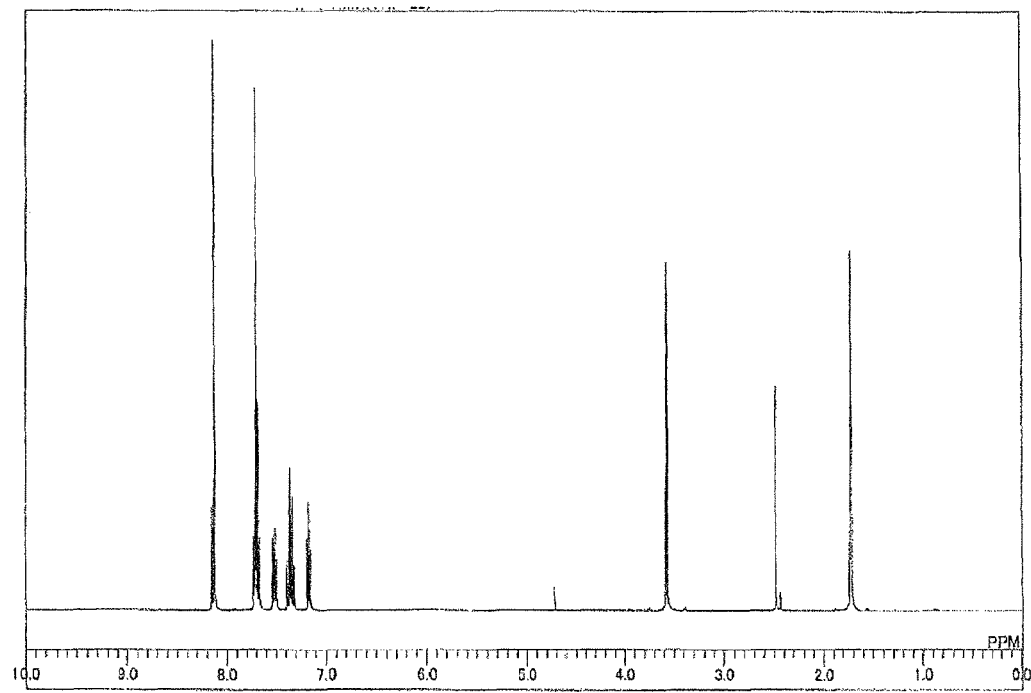
FIG. 4 shows a $^1$H-NMR chart of Compound 3-1.

Under a nitrogen atmosphere 10.0 g (0.039 mol) of Intermediate D, 39.8 g (0.20 mol) of iodobenzene, 12.4 g (0.20 mol) of copper, 21.6 g (0.16 mol) of potassium carbonate, and 200 ml of tetraglyme were heated at 190° C. with stirring for 72 hours. The reaction solution was cooled to room temperature and an inorganic matter was separated by filtration. To the remaining solution was added distilled water (200 ml) with stirring and the precipitated crystal was collected by filtration. The crystal was purified by silica gel column chromatography to give 11.9 g (75% yield) of Compound 3-1 as a white solid. APCI-TOFMS: m/z 409 [M+H]$^+$. The results of $^1$H-NMR measurement (solvent: THF-d8) are shown in FIG. 4

The materials used in the fabrication of organic EL devices in the examples are shown below.

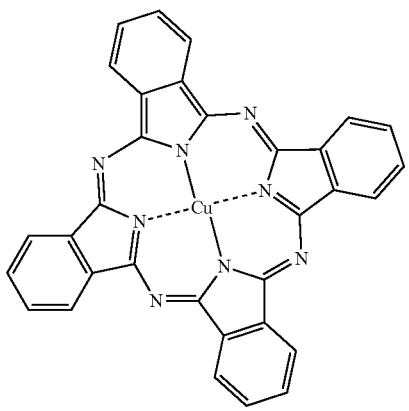
CuPc

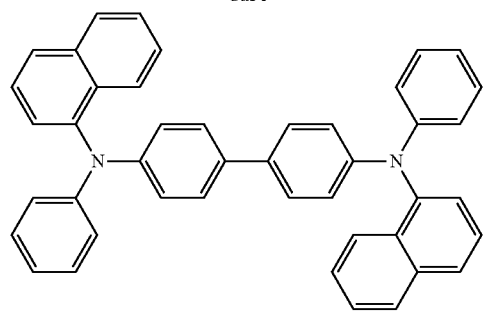
NPB

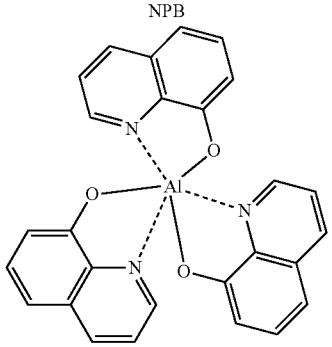
Alq3

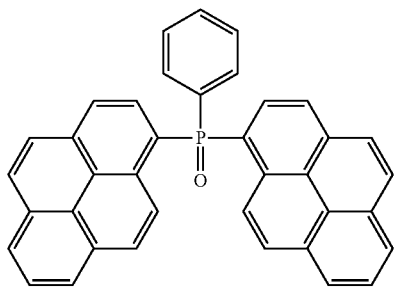
POPy2

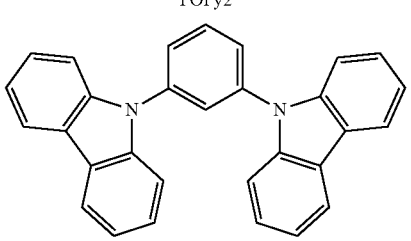
mCP

-continued

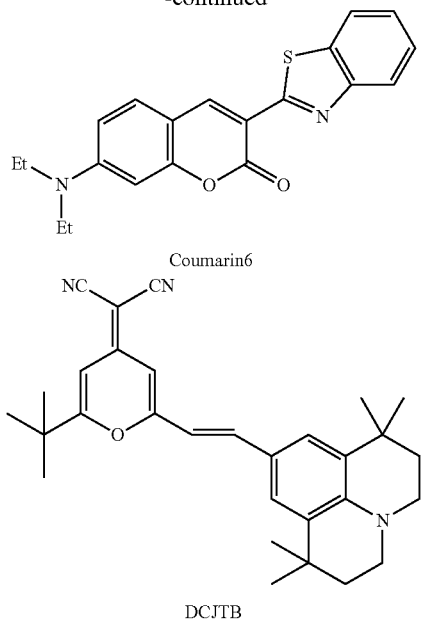

Coumarin6

DCJTB

The electron mobilities of Alq3 (host material) and POPy2 (electron-transporting material), respectively measured by the time of flight (TOF) method, are shown in Table 1. The values shown here are values obtained at an electric field of $E^{1/2}=500\ (V/cm)^{1/2}$.

TABLE 1

| Material | Electron mobility $E^{1/2} = 500(V/cm)^{1/2}$ $(cm^2/V \cdot s)$ |
|---|---|
| Alq | $1 \times 10^{-6}$ |
| POPy2 | $5 \times 10^{-5}$ |

The LUMO energies calculated by structure optimization calculation at the B3LYP/6-31G* level using Gaussian 03 are shown in Table 2.

TABLE 2

| Material | LUMO energy (eV) |
|---|---|
| Compound 1-1 | −0.63 |
| Compound 2-1 | −0.85 |
| Compound 3-1 | −1.01 |
| Alq3 | −1.73 |

The HOMO energies calculated by structure optimization calculation at the B3LYP/6-31G* level using Gaussian 03 are shown in Table 3.

TABLE 3

| Material | HOMO energy (eV) |
|---|---|
| Compound 1-1 | −4.98 |
| Compound 2-1 | −5.10 |
| Compound 3-1 | −4.84 |
| NPB | −4.71 |

Example 1

The constituent layers were deposited in thin film by the vacuum deposition process at a degree of vacuum of $4.0 \times 10^{-5}$ Pa one upon another on a glass substrate on which a 155 nm-thick ITO anode had been formed. First, CuPc was deposited on the ITO anode to a thickness of 30 nm as a hole-injecting layer and then NPB was deposited to a thickness of 20 nm as a hole-transporting layer. Next, Compound 3-1 was deposited on the hole-transporting layer to a thickness of 20 nm as an EB layer. Next, Alq3 and Coumarin 6 were co-deposited from different deposition sources to a thickness of 30 nm as a light-emitting layer. At this time, the concentration of Coumarin 6 was 0.6 wt %. Next, POPy2 was deposited to a thickness of 25 nm as an electron-transporting layer. Then, lithium fluoride (LiF) was deposited on the electron-transporting layer to a thickness of 0.5 nm as an electron-injecting layer. Finally, aluminum (Al) was deposited on the electron-injecting layer to a thickness of 100 nm as an electrode to complete the fabrication of an organic EL device.

Example 2

An organic EL device was fabricated as in Example 1 except that Compound 1-1 was used in the EB layer in Example 1.

Example 3

An organic EL device was fabricated as in Example 1 except that Compound 2-1 was used in the EB layer in Example 1.

Example 4

An organic EL device was fabricated as in Example 1 except that Compound 1-7 was used in the EB layer in Example 1.

Example 5

An organic EL device was fabricated as in Example 1 except that Compound 2-12 was used in the EB layer in Example 1.

Example 6

An organic EL device was fabricated as in Example 1 except that Compound 6-2 was used in the EB layer in Example 1.

Comparative Example 1

An organic EL device was fabricated as in Example 1 except that the thickness of the NPB layer serving as the hole-transporting layer was set at 40 nm and no EB layer was used in Example 1.

Comparative Example 2

An organic EL device was fabricated as in Example 1 except that mCP was used in the EB layer in Example 1.

Comparative Example 3

An organic EL device was fabricated as in Example 1 except that Compound 1-1 was used in the hole-transporting layer, the thickness thereof was set at 40 nm, and no EB layer was used in Example 1.

Each of the organic EL devices fabricated in Examples 1 to 6 and Comparative Examples 1 to 3 was connected to an external power source and, when direct current voltage was applied, the device was confirmed to show the luminous characteristics shown in Table 4. In Table 4, the values of the luminance, voltage, and luminous efficiency are values obtained when the device was driven by constant current at 10 mA/cm$^2$. The life characteristics show the time for attenuation of the luminance to 80% when the device was driven at an initial luminance of 2,000 cd/m$^2$.

TABLE 4

|  | Hole-transporting layer | EB layer | Initial characteristics (@10 mA/cm$^2$) | | | Life characteristics (@2000 cd/m$^2$) |
|---|---|---|---|---|---|---|
|  |  |  | Luminance [cd/m$^2$] | Voltage [V] | Luminous efficiency [lm/W] | Time for attenuation to 80% [hr] |
| Example 1 | NPB | 3-1 | 1201 | 5.9 | 6.4 | 300 |
| 2 | NPB | 1-1 | 1210 | 5.7 | 6.7 | 280 |
| 3 | NPB | 2-1 | 1174 | 5.9 | 6.3 | 270 |
| 4 | NPB | 1-7 | 1168 | 5.8 | 6.3 | 330 |
| 5 | NPB | 2-12 | 1195 | 5.8 | 6.5 | 320 |
| 6 | NPB | 6-2 | 1224 | 5.9 | 6.5 | 330 |
| Comp. example 1 | NPB | — | 1014 | 5.7 | 5.5 | 230 |
| 2 | NPB | mCP | 1283 | 6.7 | 6.0 | 180 |
| 3 | 1-1 | — | 1170 | 6.2 | 5.9 | 190 |

It is apparent from Table 4 that the luminance is improved and the luminous efficiency is enhanced in Example 1 in which a specific indolocarbazole derivative is used in the EB layer in comparison with Comparative Example 1 in which no EB layer is used. In addition, the driving life characteristics are improved. On the other hand, in Comparative Example 2 in which mCP is used, the driving voltage increases and the driving life is reduced although the luminance is improved. This proves the superiority of using the indolocarbazole derivative in the EB layer. In Comparative Example 3 in which the indolocarbazole derivative is used in the hole-transporting layer, the luminance is improved, but the driving voltage increases and the life characteristics are not improved. This indicates the effectiveness of using the indolocarbazole derivative in the EB layer. These results clearly show that the use of the aforementioned indolocarbazole derivative in the EB layer contributes to realization of an organic fluorescent EL device of high efficiency and good life characteristics.

Example 7

The constituent layers were deposited in thin film by the vacuum deposition process at a degree of vacuum of $4.0 \times 10^{-5}$ Pa one upon another on a glass substrate on which a 155 nm-thick ITO anode had been formed. First, CuPc was deposited on the ITO anode to a thickness of 30 nm as a hole-injecting layer and then NPB was deposited to a thickness of 20 nm as a hole-transporting layer. Next, Compound 1-1 was deposited on the hole-transporting layer to a thickness of 20 nm as an EB layer. Next, Alq3 and DCJTB were co-deposited from different deposition sources to a thickness of 35 nm as a light-emitting layer. At this time, the concentration of DCJTB was 0.3 wt %. Next, POPy2 was deposited to a thickness of 25 nm as an electron-transporting layer. Then, lithium fluoride (LiF) was deposited on the electron-transporting layer to a thickness of 0.5 nm as an electron-injecting layer. Finally, aluminum (Al) was deposited on the electron-injecting layer to a thickness of 100 nm as an electrode to complete the fabrication of an organic EL device.

Example 8

An organic EL device was fabricated as in Example 7 except that Compound 3-1 was used in the EB layer in Example 7.

Example 9

An organic EL device was fabricated as in Example 7 except that Compound 1-40 was used in the EB layer in Example 7.

Comparative Example 4

An organic EL device was fabricated as in Example 2 except that the thickness of the NPB layer as the hole-transporting layer was set at 40 nm and no EB layer was used in Example 2.

The luminous characteristics obtained are shown in Table 5.

Each of the organic EL devices fabricated in Examples 7 to 9 and Comparative Example 4 was connected to an external power source and, when direct current voltage was applied, the device was confirmed to show the luminous characteristics shown in Table 5. In Table 5, the values of the luminance, voltage, and luminous efficiency are values obtained when the device was driven by constant current at 10 mA/cm$^2$. The life characteristics show the time for attenuation of the luminance to 80% when the device was driven at an initial luminance of 2,000 cd/m$^2$.

TABLE 5

| | Hole-transporting layer | EB layer | Initial characteristics (@10 mA/cm²) | | | Life characteristics (@2000 cd/m²) |
| --- | --- | --- | --- | --- | --- | --- |
| | | | Luminance [cd/m²] | Voltage [V] | Luminous efficiency [lm/W] | Time for attenuation to 80% [hr] |
| Example 7 | NPB | 1-1 | 747 | 6.2 | 3.8 | 1000 |
| 8 | NPB | 3-1 | 649 | 6.6 | 3.1 | 1000 |
| 9 | NPB | 1-40 | 652 | 6.4 | 3.2 | 1200 |
| Comp. example 4 | NPB | — | 432 | 6.0 | 2.3 | 230 |

It is apparent from Table 5 that the luminance is improved and the luminous efficiency is enhanced in Examples 7, 8, and 9 in which the indolocarbazole derivative is used in the EB layer in comparison with Comparative Example 4 in which no EB layer is used. Further, the driving life characteristics are improved sharply. These results also clearly indicate the superiority of the provision of the EB layer containing the indolocarbazole derivative.

INDUSTRIAL APPLICABILITY

The indolocarbazole compound to be used in this invention exhibits good hole-transporting characteristics and has a high LUMO energy. Therefore, the provision of the EB layer containing the indolocarbazole compound between the hole-transporting layer and the fluorescent light-emitting layer so as to be adjacent to the fluorescent light-emitting layer makes it possible to transport holes effectively from the anode to the light-emitting layer and block leakage of electrons and excitons from the light-emitting layer to the hole-transporting layer. As a result, it becomes possible to enhance the luminous efficiency and improve the driving life of the device. That is, the EB layer in this invention has a function of the electron-blocking layer and/or the exciton-blocking layer and this EB layer greatly improves the initial characteristics and driving life of the organic EL device.

In addition, it has been found that the indolocarbazole compound exhibits good thin film stability and thermal stability and it has been clarified that the organic EL device having the EB layer containing the indolocarbazole compound is an organic EL device exhibiting excellent driving stability and high durability.

The organic EL device of this invention satisfies a level of performance required for practical use with respect to the luminous characteristics, driving life, and durability and is of high technical value because of its potential applicability to flat panel displays (cellular phone display devices, vehicle-mounted display devices, office computer display devices, and television sets), light sources utilizing the characteristics of planar light emitters (illumination, light sources for copying machines, and backlight sources for liquid crystal displays and meters), display boards, and marker lamps.

The invention claimed is:

1. An organic electroluminescent device comprising organic layers comprising at least a hole-injecting layer, a hole-transporting layer, and a light-emitting layer sandwiched between an anode and a cathode,
    wherein the hole-transporting layer consists essentially of one or more compounds selected from the group consisting of a triazole derivative, an oxadiazole derivative, an imidazole derivative, a carbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a thiophene oligomer; and
    wherein the light-emitting layer contains a fluorescent light-emitting material, and an electron- and/or exciton-blocking layer containing an indolocarbazole compound represented by general formula (1) is disposed between the hole-transporting layer and the light-emitting layer so as to be adjacent to the light-emitting layer:

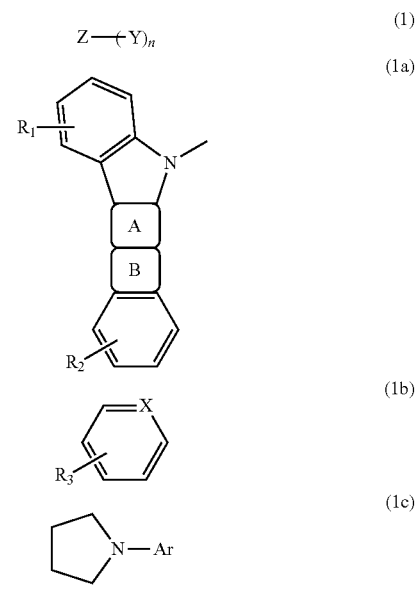

in general formula (1), Z is an n-valent aromatic hydrocarbon group of 6 to 50 carbon atoms or an n-valent aromatic heterocyclic group of 3 to 50 carbon atoms; Y is a group represented by formula (1a); n is an integer of 2 to 6; Y's may be identical with or different from each other when n is 2 or more, in formula (1a), ring A is an aromatic or heterocyclic ring fused to the adjacent rings and represented by formula (1b) and ring B is a heterocyclic ring fused to the adjacent rings and represented by formula (1c); each of $R_1$ and $R_2$ is independently a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms, in formula (1b), X is a methine group or a nitrogen atom; $R_3$ is a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; $R_3$ may be fused to a ring containing X to form a fused ring, and in formula (1c), Ar is an aromatic hydrocarbon group of 6 to 50 carbon atoms or an aromatic heterocyclic group of 3 to 50 carbon atoms, and wherein the LUMO energy of the indolocarbazole compound contained in the electron- and/or exciton-blocking layer is higher than the LUMO energy of the fluorescent light-emitting material contained in the light-emitting layer, the LUMO energy in eV of the indolocarbazole compound being greater than or equal to −1.2, and wherein the HOMO energy of the hole-transporting material contained in the hole-transporting layer is higher than the HOMO energy of the indolocarbazole compound contained in the electron- and/or exciton-blocking layer, the HOMO energy in eV of the hole-transporting material being greater than or equal to −4.8.

2. An organic electroluminescent device as described in claim 1 wherein the light-emitting layer contains a fluorescent light-emitting material and an electron-transporting host material.

3. An organic electroluminescent device as described in claim 1 wherein the indolocarbazole compound represented by general formula (1) is an indolocarbazole compound represented by the following general formula (2):

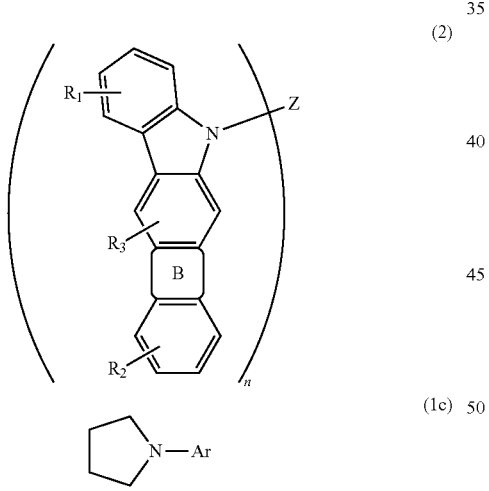

In general formula (2), ring B is a heterocyclic ring fused to the adjacent rings and represented by formula (1c); Z, Ar, $R_1$, and $R_2$ have the same meaning as those in general formula (1); $R_3$ is a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; n is an integer of 2.

4. An organic electroluminescent device as described in claim 1 wherein the indolocarbazole compound represented by general formula (1) is selected from indolocarbazole compounds represented by general formulas (3) to (6):

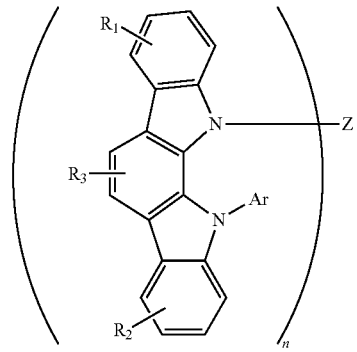

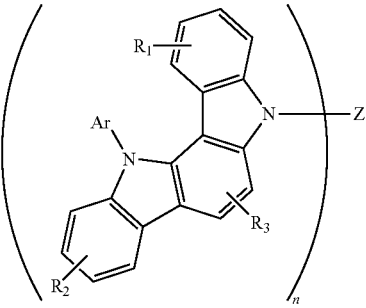

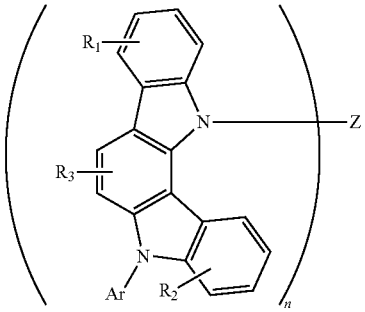

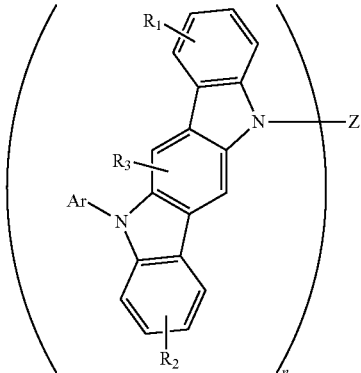

In general formulas (3) to (6), Z, Ar, $R_1$, $R_2$, $R_3$, and n have the same meaning as those in general formula (1).

5. An organic electroluminescent device as described in claim 1 wherein the organic layers further comprise an electron-transporting layer and at least one of the materials used in the said electron-transporting layer has an electron mobility of $1 \times 10^{-7}$ cm$^2$/V·s or more.

6. An organic electroluminescent device according to claim 1, wherein the hole-transporting layer consists essentially of one or more compounds selected from the group consisting of a porphyrin compound, an aromatic tertiary amine compound, and a styrylamine compound.

7. An organic electroluminescent device according to claim 1,
wherein the light-emitting layer is a single layer.

8. An organic electroluminescent device according to claim 1,
wherein the LUMO energy and the HOMO energy are determined by a structure optimization calculation at the B3LYP/6-31G* level.

9. An organic electroluminescent device according to claim 2,
wherein the electron-transporting host material has an electron transfer rate of $1\times10^{-6}$ cm$^2$/V·s or more.

* * * * *